(12) United States Patent
Ram

(10) Patent No.: US 11,000,203 B2
(45) Date of Patent: *May 11, 2021

(54) MICROELECTRONIC SENSOR FOR INTESTINAL AND GUT DIAGNOSTICS AND GUT MOTILITY MONITORING

(71) Applicant: EPITRONIC HOLDINGS PTE LTD., Singapore (SG)

(72) Inventor: Ayal Ram, Singapore (SG)

(73) Assignee: EPITRONIC HOLDINGS PTE LTD., Singapore (SG)

( * ) Notice: Subject to any disclaimer, the term of this patent is extended or adjusted under 35 U.S.C. 154(b) by 390 days.

This patent is subject to a terminal disclaimer.

(21) Appl. No.: 16/082,480

(22) PCT Filed: Mar. 7, 2017

(86) PCT No.: PCT/IB2017/051322
§ 371 (c)(1),
(2) Date: Oct. 10, 2018

(87) PCT Pub. No.: WO2017/153908
PCT Pub. Date: Sep. 14, 2017

(65) Prior Publication Data
US 2019/0076043 A1  Mar. 14, 2019

Related U.S. Application Data

(63) Continuation of application No. 15/067,093, filed on Mar. 10, 2016, now abandoned, which is a (Continued)

(51) Int. Cl.
*H01L 29/778* (2006.01)
*A61B 5/0408* (2006.01)
(Continued)

(52) U.S. Cl.
CPC .......... *A61B 5/0408* (2013.01); *A61B 1/2736* (2013.01); *A61B 3/16* (2013.01);
(Continued)

(58) Field of Classification Search
CPC . H01L 29/2003; H01L 27/20; H01L 29/7783; H01L 29/66462; H01L 27/14806;
(Continued)

(56) References Cited

U.S. PATENT DOCUMENTS 4,965,697 A   10/1990  Mosser et al.
2011/0137184 A1   6/2011  Ran et al.
(Continued)

FOREIGN PATENT DOCUMENTS

CN   1868396 A   11/2006
CN   1021947867 A   9/2011
(Continued)

OTHER PUBLICATIONS

International Search Report PCT/IB2017/051322 Completed Jun. 9, 2017; dated Jun. 21, 2017 7 pages.
(Continued)

*Primary Examiner* — Joseph A Stoklosa
*Assistant Examiner* — Brian M Antiskay
(74) *Attorney, Agent, or Firm* — The Roy Gross Law Firm, LLC; Roy Gross

(57) ABSTRACT

In some embodiments, the present application provides a swallowable capsule comprising pseudo conductive high-electron-mobility transistors (PC-HEMTs), and its use in an intestinal and gut diagnostics and gut motility monitoring.

28 Claims, 23 Drawing Sheets
(18 of 23 Drawing Sheet(s) Filed in Color)

Related U.S. Application Data continuation of application No. 15/157,285, filed on May 17, 2016, now abandoned.

(60) Provisional application No. 62/384,831, filed on Sep. 8, 2016.

(51) Int. Cl.

| | |
|---|---|
| *H01L 29/205* | (2006.01) |
| *H01L 29/20* | (2006.01) |
| *A61B 5/00* | (2006.01) |
| *A61B 5/04* | (2006.01) |
| *A61B 5/0452* | (2006.01) |
| *A61B 3/16* | (2006.01) |
| *A61B 1/273* | (2006.01) |
| *A61B 5/0478* | (2006.01) |
| *A61B 7/04* | (2006.01) |
| *G01N 27/414* | (2006.01) |
| *A61B 5/08* | (2006.01) |
| *A61B 5/11* | (2006.01) |
| *A61B 5/021* | (2006.01) |
| *A61B 5/05* | (2021.01) |

(52) U.S. Cl.
CPC ........ *A61B 5/0006* (2013.01); *A61B 5/04017* (2013.01); *A61B 5/0452* (2013.01); *A61B 5/0478* (2013.01); *A61B 7/045* (2013.01); *G01N 27/414* (2013.01); *H01L 29/2003* (2013.01); *H01L 29/205* (2013.01); *H01L 29/7786* (2013.01); *A61B 5/002* (2013.01); *A61B 5/021* (2013.01); *A61B 5/05* (2013.01); *A61B 5/08* (2013.01); *A61B 5/1102* (2013.01); *A61B 5/1107* (2013.01); *A61B 5/681* (2013.01); *A61B 5/7225* (2013.01); *A61B 2562/164* (2013.01)

(58) Field of Classification Search
CPC ........... H01L 29/42316; H01L 21/8252; H01L 29/66212; H01L 29/872
USPC ................ 600/300, 302, 372, 382–393, 593; 607/133
See application file for complete search history.

(56) References Cited

U.S. PATENT DOCUMENTS

| | | |
|---|---|---|
| 2011/0152639 A1 | 6/2011 | Mattut |
| 2014/0323895 A1 | 10/2014 | Vitushinsky et al. |

FOREIGN PATENT DOCUMENTS

| | | |
|---|---|---|
| JP | 2008047767 A | 2/2008 |
| KR | 100856460 B1 | 9/2008 |
| TW | 1344205 B | 6/2011 |

OTHER PUBLICATIONS

Written Opinion of the International Searching Authority PCT/IB2017/051322 dated Jun. 21, 2017 11 pages.

$V_G \gg V_T$ $V_G = 0$
$V_G > V_T$ $V_G \ll V_T$

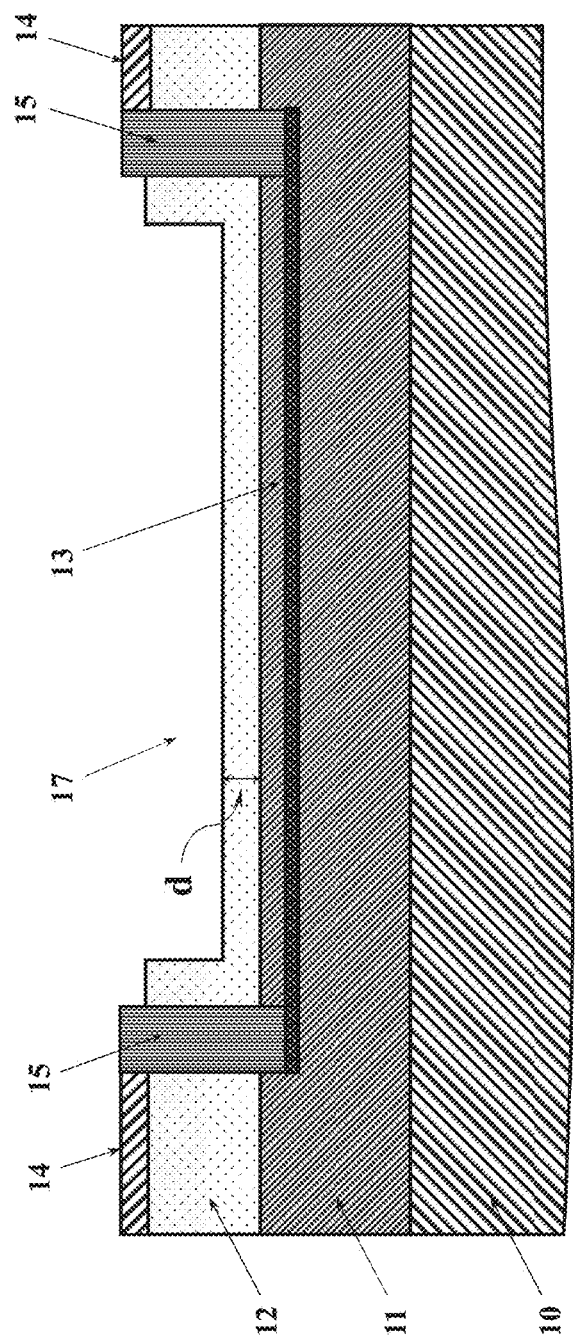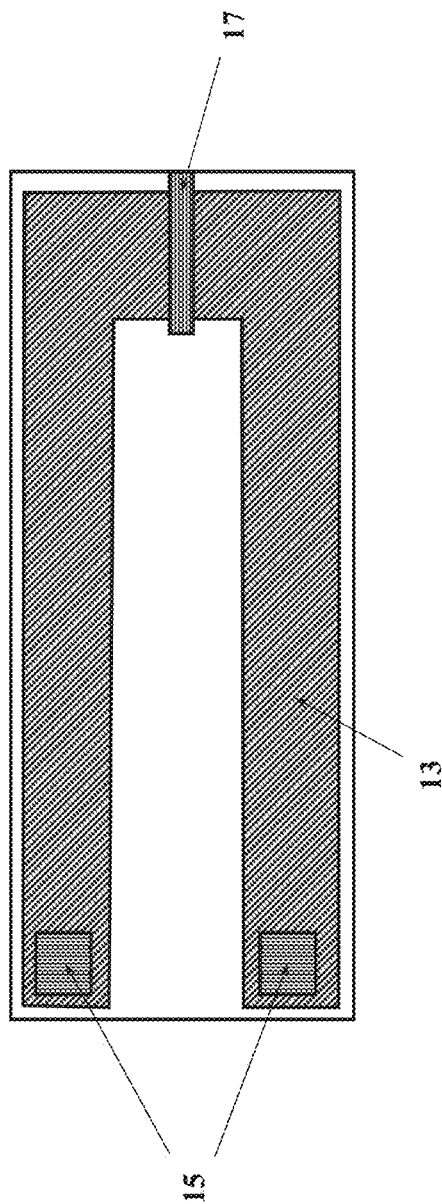

Fig. 5a          Ga-Face Polarity
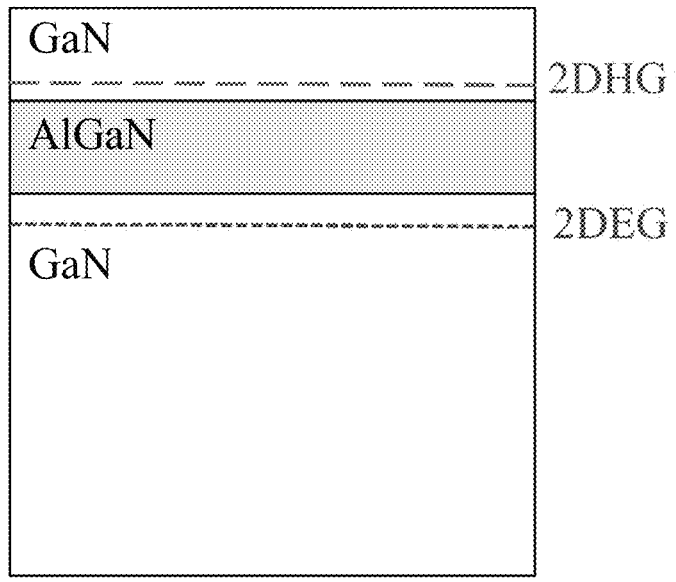
Fig. 5b          N-Face Polarity
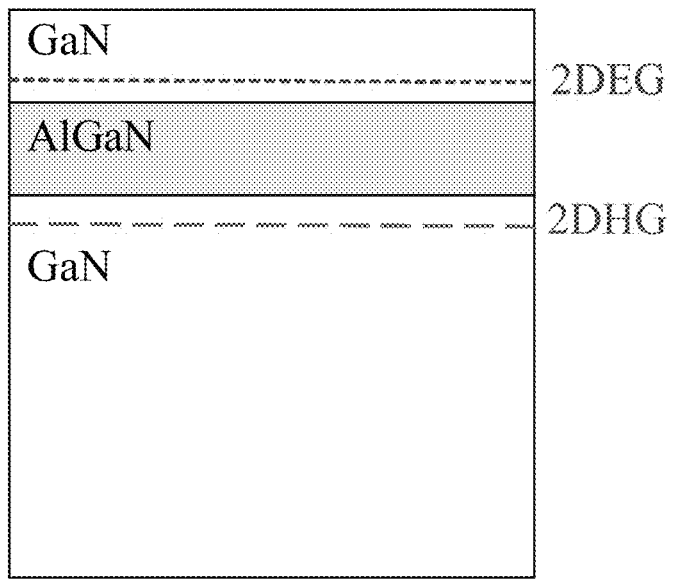

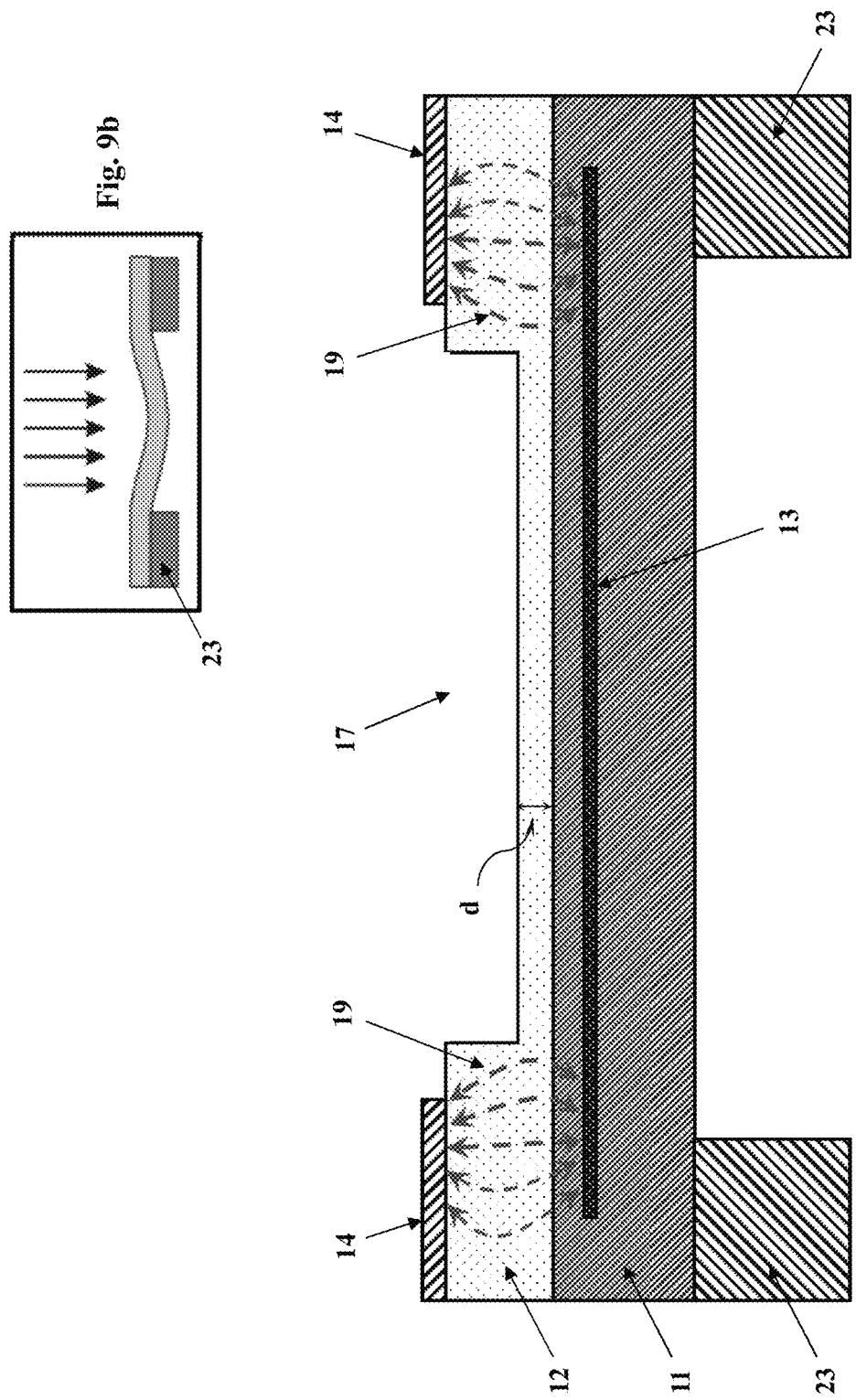

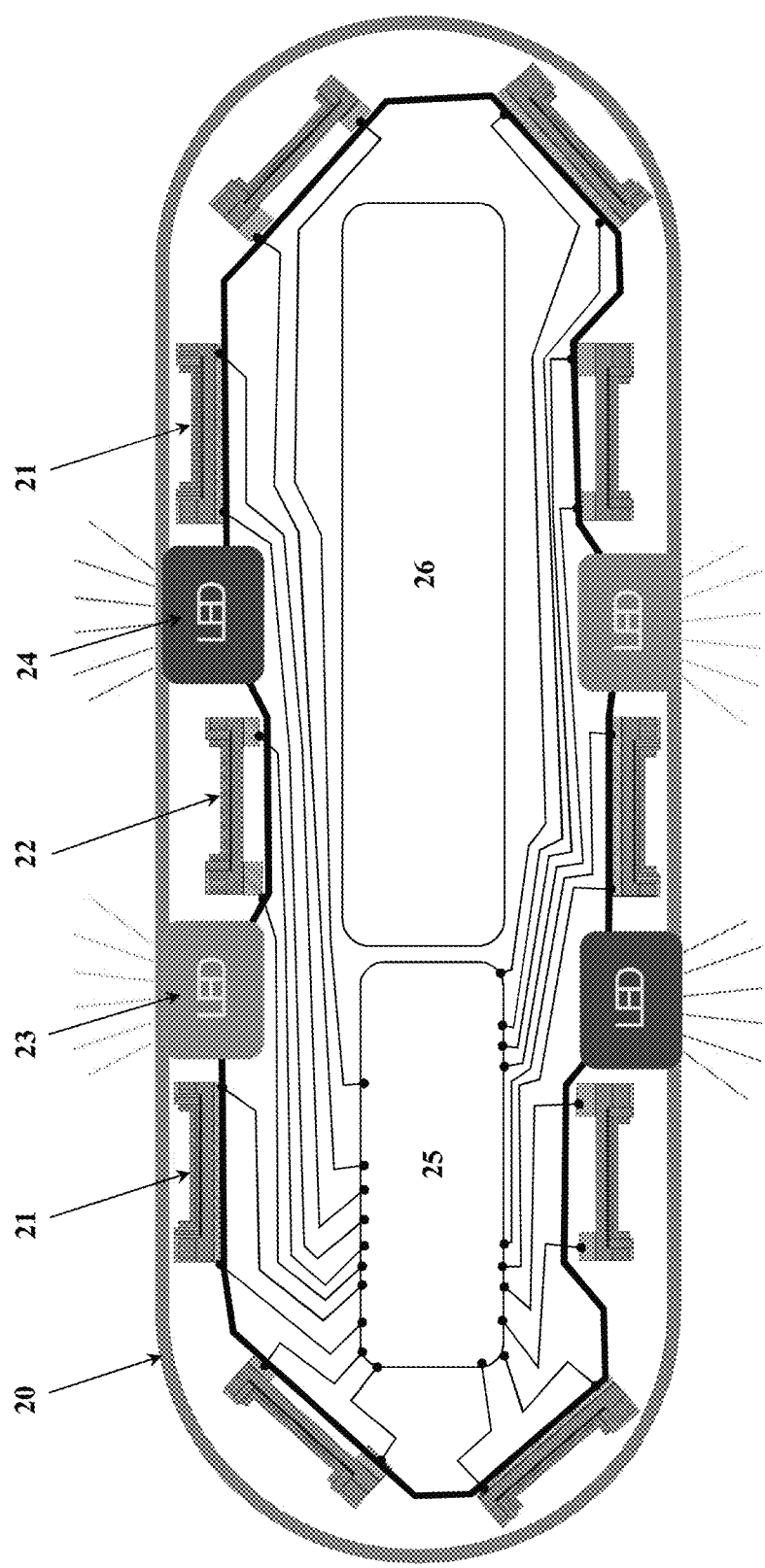

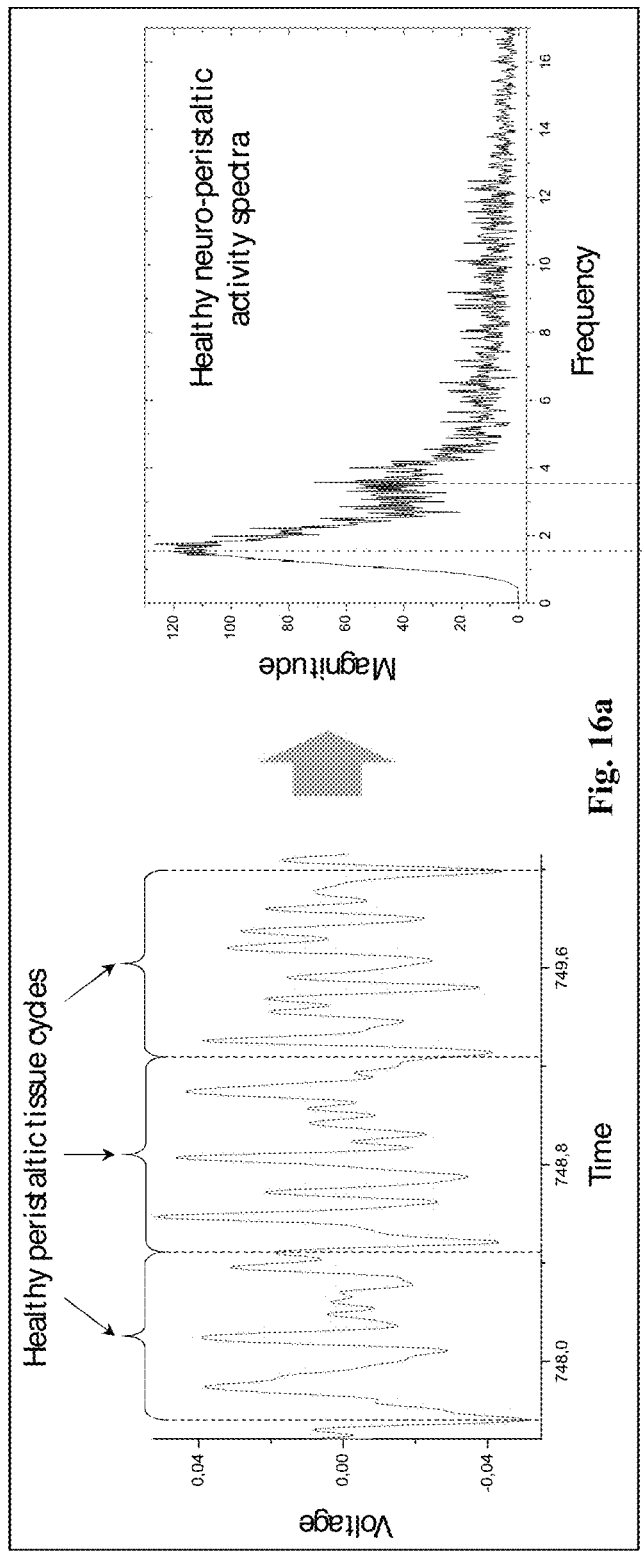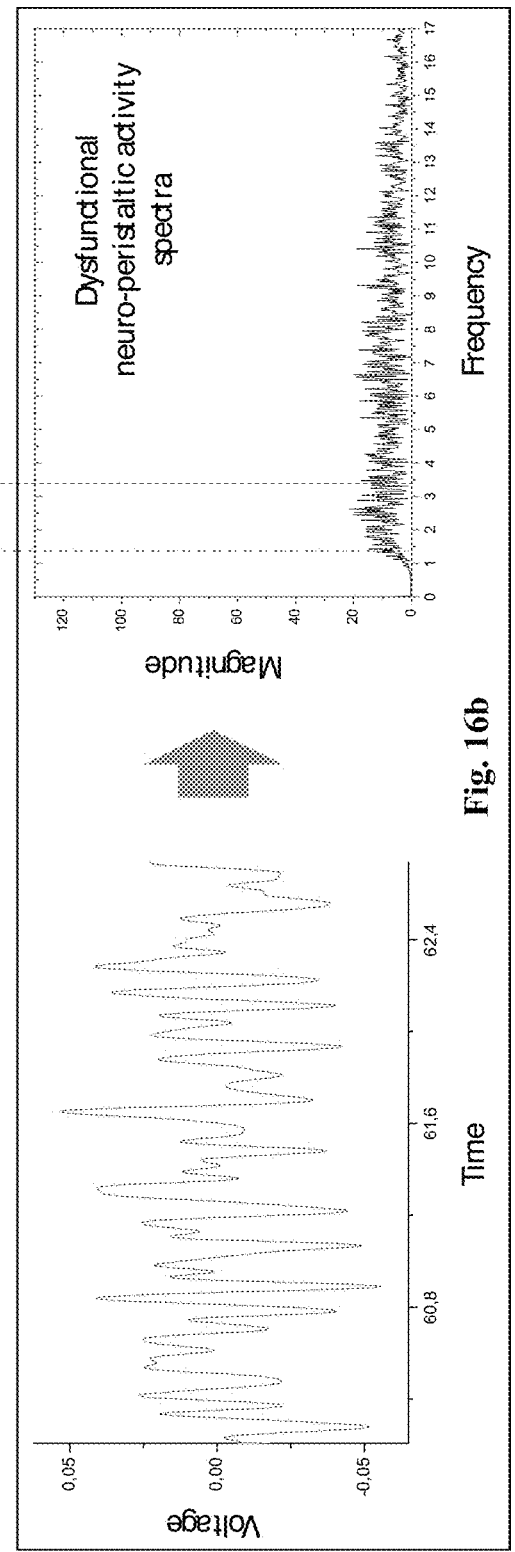
Fig. 16a
Fig. 16b

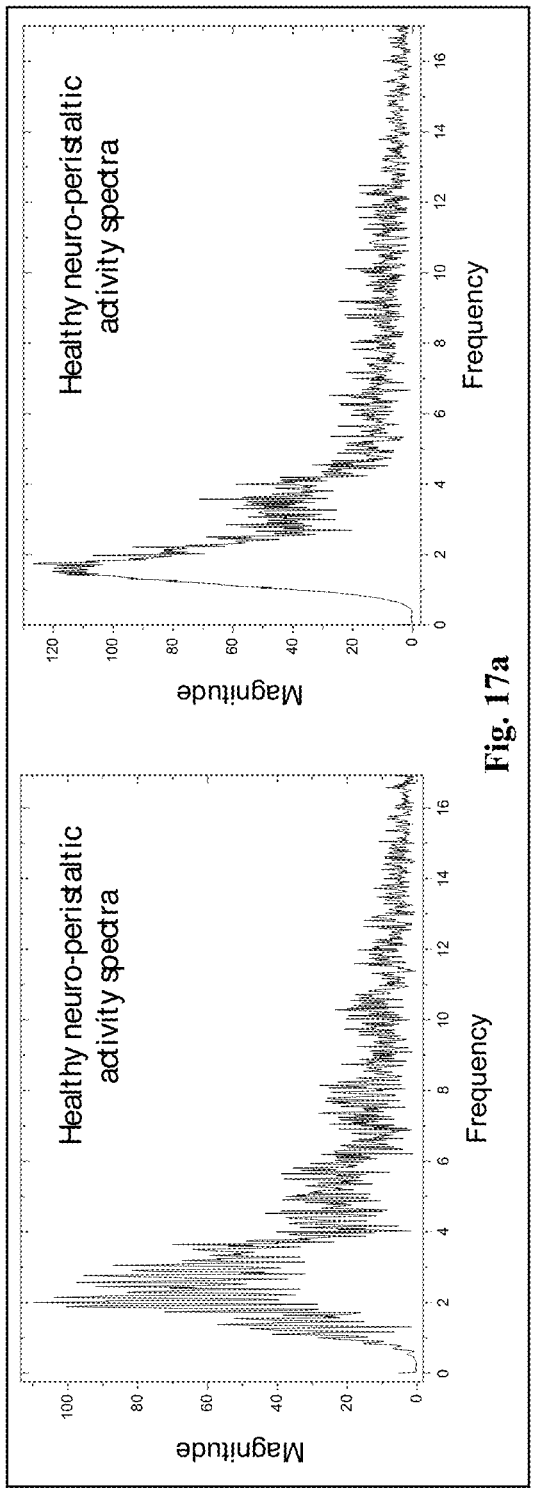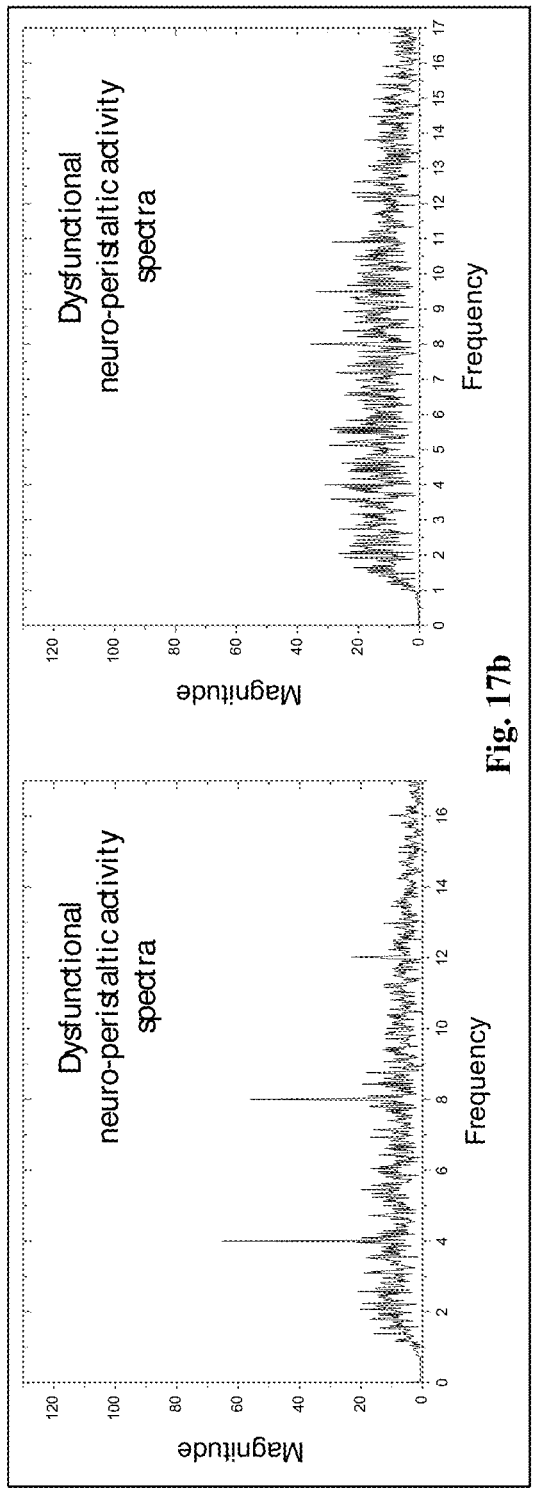
Fig. 17a
Fig. 17b

MICROELECTRONIC SENSOR FOR INTESTINAL AND GUT DIAGNOSTICS AND GUT MOTILITY MONITORING

RELATED APPLICATIONS

This application is a National Phase of PCT Patent Application No. PCT/IB2017/051322 having International filing date of Mar. 7, 2017, which claims the benefit of priority of U.S. patent application Ser. No. 15/067,093 filed on Mar. 10, 2016, U.S. patent application Ser. No. 15/157,285 filed on May 17, 2016, and U.S. Provisional Application No. 62/384,831 filed on Sep. 8, 2016. The contents of the above applications are all incorporated by reference as if fully set forth herein in their entirety.

TECHNICAL FIELD

The present application relates to the field of microelectronic sensors and their use in monitoring of physiological parameters of a human body. In particular, the present application relates to the open-gate pseudo-conductive high-electron-mobility transistors and their use in intestinal and gut diagnostics and gut motility monitoring.

BACKGROUND

Various intestinal and gut disorders, including esophageal reflux are well-known and annoying conditions and usually express as a chronic heartburn, with many people suffering from it. The heartburn is characterized by several symptoms including chest pain, indigestion, or bitter-tasting fluids in the throat or mouth more than twice a week. These chronic symptoms can interfere with daily activities and may be associated with gastroesophageal reflux disease, which can damage the esophagus and lead to more serious problems, such as tumour growth developing into cancerogenic neoplasms within the colon, small intestine and stomach. These malignomas locally cause dysfunctions of the peristalsis and neuronal signalling. Because gastroesophageal reflux disease and other esophageal conditions are hard to diagnose from symptoms alone, reflux and gut pressure monitoring may be a good way for doctors to evaluate these symptoms. By identifying the frequency and duration of the reflux, doctors can decide on a proper treatment. Therefore, the continuous and real-time sensing of the intestinal and gut, including determination of the gut pressure and the frequency and duration of the reflux are very important.

The most advanced solution in the in-vivo intestinal and gut diagnostics today is the use of autonomous capsule devices for capturing images. These capsules typically contain a small battery and various photographic capabilities for capturing images of the intestinal tract. One type of such capsules is described in U.S. Pat. No. 5,604,531. For exemplary purposes, a typical capsule has an elongated form and is about the size of a large pharmaceutical capsule or pill.

After swallowing, the autonomous capsule passes through the gastro-intestinal tract transmitting images to a recorder mounted in a belt-like device worn by the subject. This capsule is capable of capturing an image every half a second and provides a real-time diagnostics solution to medical doctors. The images can be optionally reviewed at a later date. An example of such capsule is the PILLCAM™ marketed by Given Imaging Ltd.

The present application is a step forward from the above imaging capsules and suggests replacing the imaging capabilities of the capsules with the ultrasensitive sensing of the intestinal and gut and measuring internal pressure within the esophagus and in both the rectum and anal sphincters. This is a non-obvious solution simply because there have been no such blindly sensing autonomous capsules known or disclosed until now. In order to conduct such ultrasensitive diagnostics with the capsules of the application, the present inventors proposed to encapsulate the sensors based on the GaN/AlGaN pseudo-conductive high-electron-mobility transistors in the capsules. This will allow physicians to detect and monitor the growth of tumours and to evaluate causes of gastric reflux, difficulty swallowing, functional chest including other pre-operative evaluations with no need for imaging.

The polarization doped high-electron-mobility transistor (HEMT) is a field effect transistor (FET) in which two layers of different bandgap and polarisation field are grown upon each other forming a hetero-junction structure. As a consequence of the discontinuity in the polarisation field, surface charges are created at the interface between the layers of the hetero-junction structure. If the induced surface charge is positive, electrons will tend to compensate the induced charge resulting in the formation of the channel. Since in the HEMT, the channel electrons are confined in a quantum well in an infinitely narrow spatial region at the interface between the layers, these electrons are referred to as a two-dimensional electron gas (2DEG). This special confinement of the channel electrons in the quantum well actually grants them two-dimensional features, which strongly enhance their mobility surpassing the bulk mobility of the material in which the electrons are flowing.

The HEMTs based on the layers of III-V semiconductor materials, such as gallium nitride (GaN) and aluminium gallium nitride (AlGaN), have recently been developed with a view to high-voltage and high-power switching applications. The high voltages and high switching speeds allow smaller, more efficient devices, such as home appliances, communications and automobiles to be manufactured. To control the density of electrons in the 2DEG channel and to switch the HEMT on and off, the voltage at the gate of the transistor should be regulated.

FIGS. 1a-1c schematically shows the quantum well at three different biasing conditions starting from the positive gate potential ($V_G$), much higher than the threshold voltage ($V_T$), and going down to the 0V gate potential and further to the negative values below the threshold voltage. The $V_T$ is defined as a voltage required to populate electrons at the interface between the GaN and AlGaN layers, thereby creating conductivity of the 2DEG channel. Since the 2DEG channel electrons occupy energy levels below the Fermi level, the Fermi level in a quantum well is located above several energy levels when $V_G \gg V_T$ (FIG. 1a). This enables high population of the 2DEG channel electrons and hence, high conductivity. The HEMT is turned on in this case. However, when $V_G$ decreases to 0V (FIG. 1b), the Fermi level also drops with respect to the quantum well. As a result, much fewer electron energy levels are populated and the amount of the 2DEG channel electrons significantly decreases. When $V_G \ll V_T$ (FIG. 3c), all electron energy levels are above the Fermi level, and there is no 2DEG electrons below the gate. This situation is called "channel depletion", and the HEMT is turned off.

Many commercially available AlGaN/GaN-based HEMT structures have a negative $V_T$, resulting in a "normally-on" operation mode at 0V gate potential. They are called "depletion-mode transistors" and used in various power switching applications when the negative voltage must be applied on the gate in order to block the current. However, for safe operation at high voltage or high power density, in order to reduce the circuit complexity and eliminate standby power consumption, HEMTs with "normally-off" characteristics are preferred.

Several techniques to manufacture the normally-off HEMTs have been reported. Burnham et al (2010) proposed normally-off structures of the recessed gate type. In this structure, the AlGaN barrier layer is etched and the gate is brought closer to the interface between the AlGaN barrier layer and the GaN buffer layer. As the gate approaches the interface between the layers, the $V_T$ increases. The normally-off operation of the transistor is achieved once the depletion region reaches the interface and depletes the 2DEG channel at zero gate voltage. The major advantages of these HEMTs are relatively lower power consumption, lower noise and simpler drive circuits. These HEMTs are currently used, for example, in microwave and millimetre wave communications, imaging and radars.

Chang et al (2009) proposed instead of etching the relatively thick barrier layer to approach the AlGaN/GaN interface, to use a very thin AlGaN barrier. This structure also achieves normally-off operation by approaching the gate towards the AlGaN/GaN interface. Chen et al (2010) proposed to use the fluorine-based plasma treatment method. Although many publications have adopted various methods to achieve normally-off devices with minimum impact on the drain current, they unfortunately sacrificed device turn-on performance.

SUMMARY

The present application describes embodiments of a method for monitoring physiological parameters of a human subject using a microelectronic sensor based on an open-gate pseudo-conductive high-electron mobility transistor (PC-HEMT). In some embodiments, a transistor comprises a substrate, on which a multilayer hetero-junction structure is deposited. This hetero-junction structure may comprise at least two layers, a buffer layer and a barrier layer, which are grown from III-V single-crystalline or polycrystalline semiconductor materials.

A conducting channel comprising a two-dimensional electron gas (2DEG), in case of two-layers configuration, or a two-dimensional hole gas (2DHG), in case of three-layers configuration, is formed at the interface between the buffer and barrier layers and provides electron or hole current in the system between source and drain electrodes. The source and drain, either ohmic or capacitively-coupled (non-ohmic) contacts are connected to the formed 2DEG/2DHG channel and to electrical metallizations, the latter are placed on top of the transistor and connect it to the sensor system. An optional dielectric layer is deposited on top of the hetero-junction structure. The open gate area of the transistor is formed between the source and drain areas as a result of recessing or growing of the top layer to a specific thickness.

If the source and drain contacts are non-ohmic (capacitively-coupled), in order to electrically contact the 2DEG/2DHG channel underneath, which is about 5-20 nm bellow metallizations, the AC-frequency regime is used. The capacitive coupling of the non-ohmic metal contacts with the 2DEG/2DHG channel is normally induced at the frequency higher than 30 kHz. In the case of non-ohmic contacts, the DC readout cannot be carried out. Instead, the AC readout or impedance measurements of the electric current flowing through the 2DEG/2DHG-channel are performed.

In some embodiments, the significant features of the PC-HEMT structure are that:
(i) the thickness of the top layer in the open gate area between the source and drain contacts is 5-9 nm, preferably 6-7 nm, more preferably 6.3 nm, and that corresponds to the pseudo-conducting current range between normally-on and normally-off operation mode of the transistor,
(ii) the surface of the top layer within the open gate area between the source and drain contacts has a roughness of about 0.2 nm or less, preferably 0.1 nm or less, more preferably 0.05 nm, and
(iii) the non-ohmic source and drain contacts for the capacitive coupling with the conductive 2DEG/2DHG channel optionally replace the ohmic contacts.

In some embodiments, the PC-HEMT multilayer heterojunction structure of the present application is grown from any available III-V single-crystalline or polycrystalline semiconductor materials, such as GaN/AlGaN, GaN/AlN, GaN/InN, GaN/InAlGaN, GaAs/AlGaAs GaN/InAlN, InN/InAlN, and $LaAlO_3/SrTiO_3$. In case of the GaN/AlGaN PC-HEMT, it has been surprisingly found that in the open gate area of the PC-HEMT, the thickness of the top layer that corresponds to the pseudo-conducting current range between normally-on and normally-off operation mode of the PC-HEMT, is about 6-7 nm.

In a particular embodiment, the hetero-junction structure may be a three-layer structure consisting of two buffer layers and one barrier layer squeezed between said buffer layers like in a sandwich. This may lead to formation of the two-dimensional hole gas (2DHG) in the top buffer layer above the barrier layer which results in reversing polarity of the transistor.

In some embodiments, the heterojunction structure is placed on a free-standing membrane providing an additional mass-loading effect on the sensor surface and allowing a pressure sensing mode of the sensor. In some embodiments, the present application provides the PC-HEMT-based microelectronic sensor for an intestinal and gut diagnostics and gut motility monitoring in a form of a swallowable capsule or pill.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Disclosed embodiments will be understood and appreciated more fully from the following detailed description taken in conjunction with the appended figures.

FIG. 1 illustrates a theory behind the 2DEG formation (charge neutrality combined with the lowest energy level) at the conduction band discontinuity and schematically shows the quantum well at three different biasing conditions:

FIG. 4a schematically shows a side (XZ) cross-sectional view of the PC-HEMT of an embodiment without a dielectric layer.

FIG. 4b schematically shows a top (XY) cross-sectional view of the PC-HEMT of an embodiment without a dielectric layer.

FIG. 5a schematically shows the formation of the 2DEG and 2DHG conducting channels in the Ga-face three-layer GaN/AlGaN/GaN PC-HEMT structure.

FIG. 5b schematically shows the formation of the 2DEG and 2DHG conducting channels in the N-face three-layer GaN/AlGaN/GaN PC-HEMT structure.

FIG. 9a schematically shows a cross-sectional view of the PC-HEMT of an embodiment with free-standing membranes.

FIG. 9b illustrates a situation when the external pressure (mass effect) is applied on the sensor incorporating the PC-HEMT of FIG. 8a, and transferred into a changed internal strain caused by bending.

FIG. 10a schematically shows a design of the autonomous capsule for in-vivo sensing of an intestine and gut.

FIG. 16a shows the results of the single-point non-invasive measurements of a mouse gut without a medicament supply.

FIG. 16b shows the results of the single-point non-invasive measurements of a mouse gut with a medicament supply.

FIG. 17a shows two Fourier spectra recorded with the PC-HEMT-based sensor of an embodiment from the gut of a mouse without the medicaments added.

FIG. 17b shows the Fourier spectra recorded with the PC-HEMT-based sensor of an embodiment with the addition of nifedipin and lidocaine for deactivation of a muscle and neuronal activity.

DETAILED DESCRIPTION

Figure 1A:
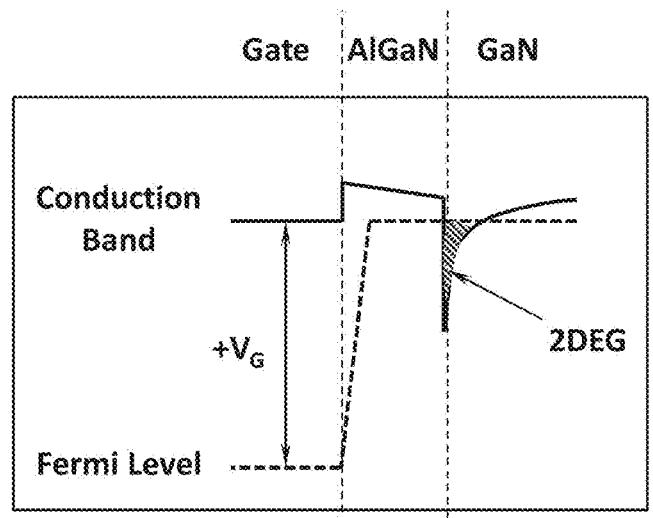
FIG. 1a shows the positive gate potential ($+V_G$), much higher than the threshold voltage ($V_T$)
Figure 1B:
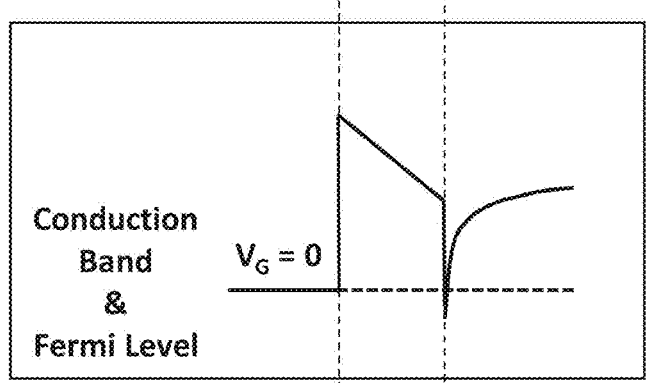
FIG. 1b shows the zero gate potential.
Figure 1C:
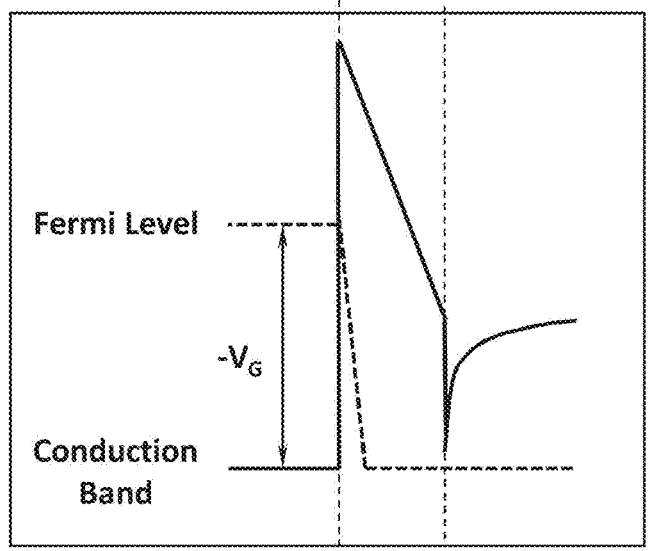
FIG. 1c shows the negative gate potential ($-V_G$) below the threshold voltage ($V_T$).

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. As used herein, the term "about" means there is a 10% tolerance of the mentioned or claimed value. As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

In brief, the working principle of the PC-HEMT sensor is based on ultra-high charge sensitivity at the sensor surface as described in details in the co-pending patent application U.S. Ser. No. 15/067,093 and U.S. Ser. No. 15/157,285, from which the present application claims priority. For example, an intestine or a gut physically represents a volume source of an electric dipole field acting within a volume electrolytic conductor represented by human body. Using the enormously high charge sensitivity, it is possible to record the movement of the intestine and gut as a certain wave (dynamic distribution) of a charge cycling at the sensor's surface.

Figure 2:
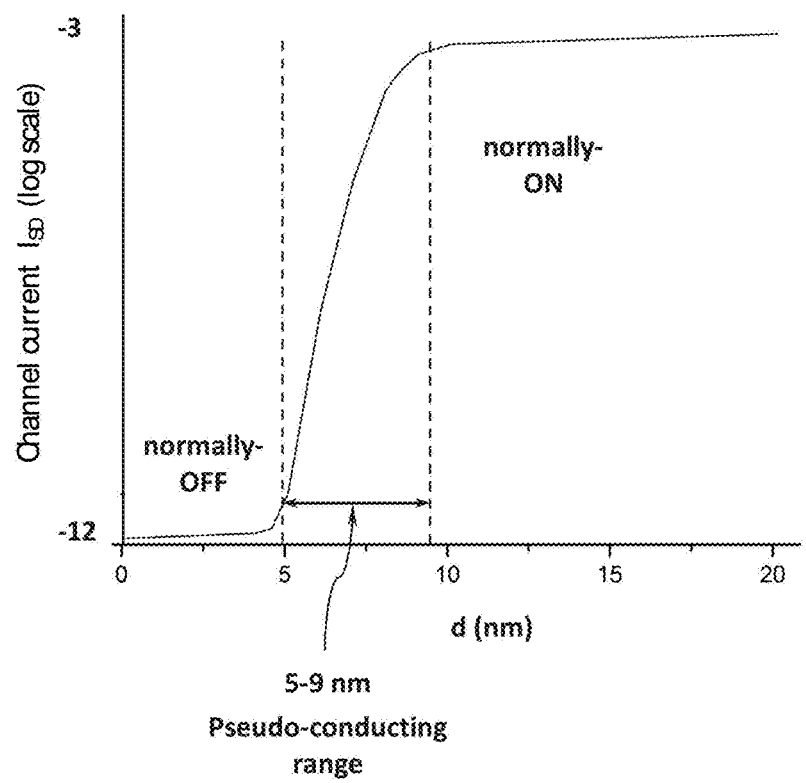
FIG. 2 schematically shows the dependence of the source-drain current (a charge carrier density) induced inside the 2DEG channel of a GaN/AlGaN HEMT on the thickness of the AlGaN barrier layer recessed in the open gate area.

FIG. 2 shows the dependence of the source-drain current (a charge carrier density) on the recessed barrier layer thickness. As seen from the plot, structures that have a thickness of the barrier layer larger than 9 nm form normally-on 2DEG channels. In such structures, due to the inherent polarisation effects present in the III-V materials, a thin sheet of charges is induced at the top and bottom of the interfaces of the barrier layer. As a result, a high electric field is induced in the barrier layer, and surface donor states at the top interface start donating electrons to form the 2DEG channel at the proximity of the hetero-junction interface without the application of a gate bias. These structures therefore constitute normally-on devices. On contrast, the structures that have a thickness of the barrier layer lower than about 5 nm constitute normally-off devices.

The barrier layer recessed or grown to 5-9 nm is optimised for significantly enhancing sensitivity of the sensor. This thickness of the barrier layer corresponds to the "pseudo-conducting" current range between normally-on and normally-off operation modes of the 2DEG channel and requires further explanation.

"Pseudo-contacting" current range of the 2DEG channel is defined as an operation range of the channel between its normally-on and normally-off operation modes. "Trap states" are states in the band-gap of a semiconductor which trap a carrier until it recombines. "Surface states" are states caused by surface reconstruction of the local crystal due to surface tension caused by some crystal defects, dislocations, or the presence of impurities. Such surface reconstruction often creates "surface trap states" corresponding to a surface recombination velocity. Classification of the surface trap states depends on the relative position of their energy level inside the band gap. The surface trap states with energy above the Fermi level are acceptor-like, attaining negative charge when occupied. However, the surface trap states with energy below the Fermi level are donor-like, positively charged when empty and neutral when occupied. These donor-like surface trap states are considered to be the source of electrons in the formation of the 2DEG channel. They may possess a wide distribution of ionization energies within the band gap and are caused by redox reactions, dangling bonds and vacancies in the surface layer. A balance always exists between the 2DEG channel density and the number of ionised surface donors which is governed by charge neutrality and continuity of the electric field at the interfaces.

Thus, the donor-like surface traps at the surface of the barrier layer are one of the most important sources of the 2DEG in the channel. However, this only applies for a specific barrier layer thickness. In a relatively thin barrier layer, the surface trap state is below the Fermi level. However, as the barrier layer thickness increases, the energy of the surface trap state approaches the Fermi energy until it coincides with it. The thickness of the barrier layer corresponding to such situation is defined as "critical". At this point, electrons filling the surface trap state are pulled to the channel by the strong polarisation-induced electric field found in the barrier to form the 2DEG instantly.

If the surface trap states are completely depleted, further increase in the barrier layer thickness will not increase the 2DEG density. Actually, if the 2DEG channel layer fails to stretch the barrier layer, the later will simply relax. Upon relaxation of the barrier layer, many crystal defects are created at the interface between the buffer and barrier layers, and the piezoelectric polarisation instantly disappears causing deterioration in the 2DEG density.

Figure 3:
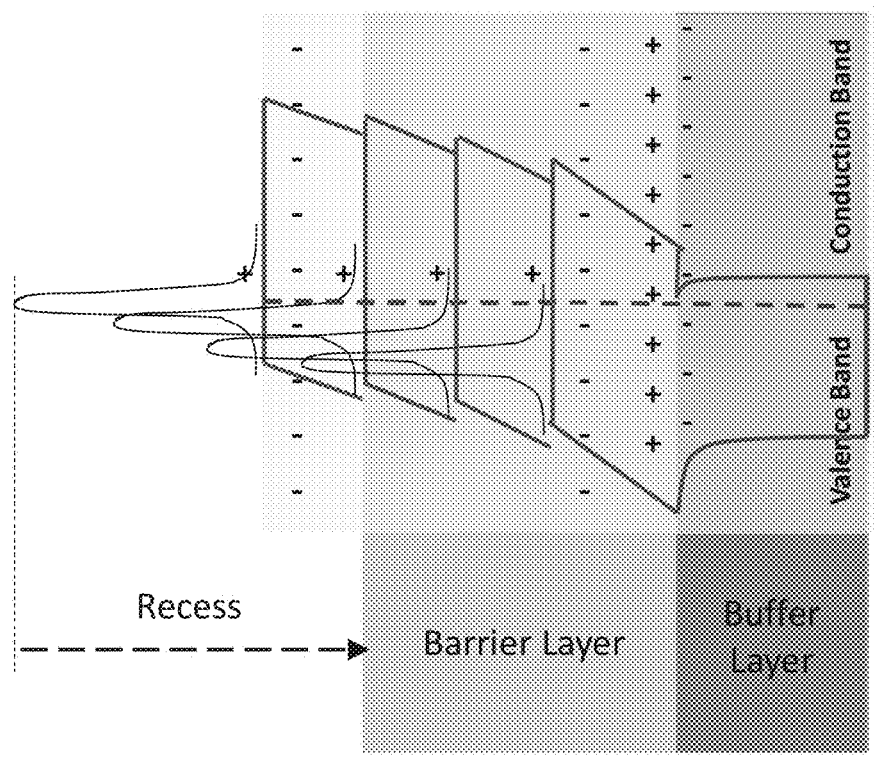
FIG. 3 illustrates a theory behind the 2DEG formation (charge neutrality combined with the lowest energy level) at the conduction band discontinuity.

In order to illustrate the above phenomenon of the pseudo-conducting current, reference is now made to FIG. 3. Energy equilibrium between the donor surface trap states and the AlGaN tunnel barrier leads to the 2DEG formation (charge neutrality combined with the lowest energy level) at the conduction band discontinuity. As shown above, the decrease in the thickness of the barrier layer results in increase of the energy barrier. As a result, the ionisable donor-like surface trap states, which are responsible for electron tunnelling from the surface to 2DEG, drift bellow the Fermi level, thereby minimizing the electron supply to the 2DEG channel. This theoretical situation is shown in FIG. 3. Therefore, the recess of the AlGaN layer from 9 nm to 5 nm leads to huge drop in conductivity of the two-dimensional electron gas for six orders of magnitude.

Thus, the mechanism of the 2DEG depletion based on recessing the barrier layer is strongly dependent on the donor-like surface trap states (or total surface charge). As the thickness of the barrier layer decreases, less additional external charge is needed to apply to the barrier layer surface in order to deplete the 2DEG channel There is a critical (smallest) barrier thickness, when the 2DEG channel is mostly depleted but still highly conductive due to a combination of the energy barrier and the donor surface trap states energy. At this critical thickness, even the smallest energy shift at the surface via any external influence, for example an acoustic wave propagating along the surface, leads immediately to the very strong 2DEG depletion. As a result, the surface of the barrier layer at this critical thickness is extremely sensitive to any smallest change in the electrical field of the surroundings.

In light of the above, it is possible to conclude that the recess of the barrier layer from 9 nm down to 5 nm significantly reduced the 2DEG density, brought the sensor to the "near threshold" operation and resulted in highly increased surface charge sensitivity. The specific 5-9 nm thickness of the barrier layer responsible for the pseudo-conducting behaviour of the 2DEG channel gives the sensor an incredible sensitivity.

Further, the recessed or grown barrier layer thickness, roughness of the barrier layer surface is another very important parameter that has not been previously disclosed. It has been surprisingly found that that the roughness of the AlGaN barrier layer surface bellow 0.2 nm prevents scattering of the donor-like surface trap states. Thus, combination of these two features: 5-9 nm thickness of the AlGaN barrier layer and strongly reduced roughness of its surface make the sensor incredibly sensitive.

In one embodiment, FIGS. 4a and 4b show two cross-sectional views (side and top) of the PC-HEMT configuration of the present application comprising:
- a multilayer heterojunction structure made of III-V single-crystalline or polycrystalline semiconductor materials, said structure comprising a buffer layer (11) and a top barrier layer (12), and being deposited on a substrate layer (10);
- a two-dimensional electron gas (2DEG) conducting channel (13) formed at the interface between said buffer layer (11) and said top barrier layer (12) and providing electron current in said transistor between source and drain ohmic contacts (15);
- the source and drain ohmic contacts (15) connected to said 2DEG conducting channel (13) and to electrical metallizations (14) for connecting said transistor to an electric circuit; and
- an open gate area (17) between said source and drain ohmic contacts (15);

wherein:
- (i) the thickness (d) of said barrier layer (12) in said open gate area (17) is in the range of 5-9 nm, which corresponds to the pseudo-conducting current range between normally-on and normally-off operation mode of the transistor, and
- (ii) the surface of said barrier layer (12) has a roughness of about 0.2 nm or less.

Figure 4C:
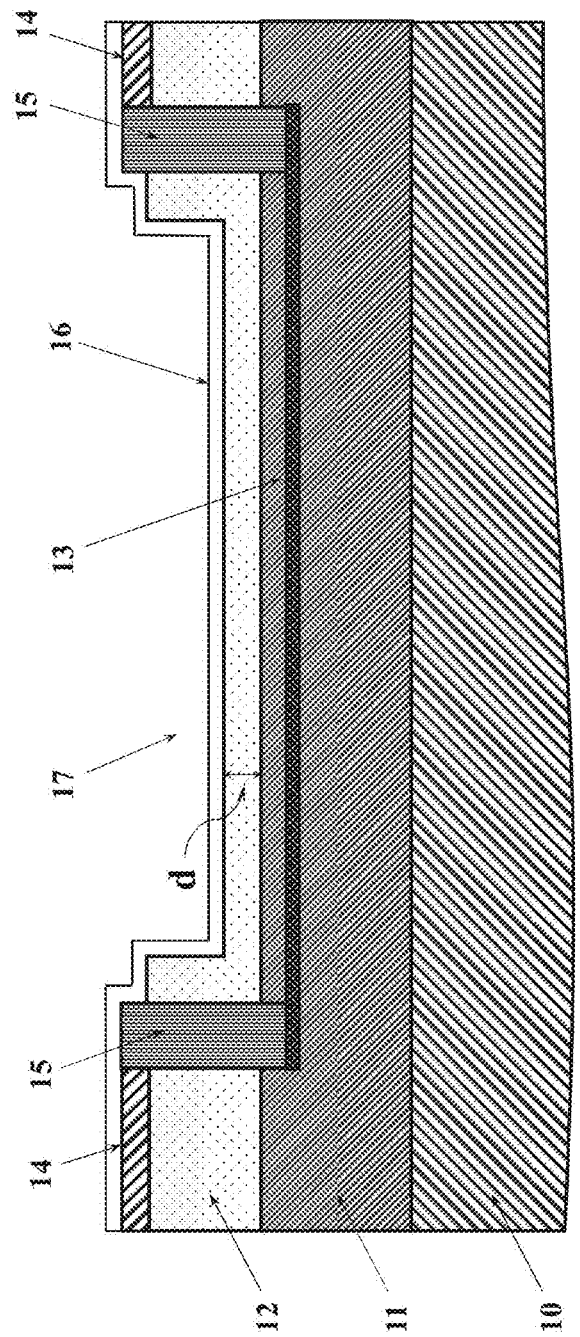
FIG. 4c schematically shows a cross-sectional view of the PC-HEMT of an embodiment with a dielectric layer.

The same transistor as in FIGS. 4a and 4b, but further comprising a dielectric layer (16) deposited on top of said barrier layer (12), is schematically shown in FIG. 4c. The optional dielectric layer (16), which is used for device passivation, is made, for example, of SiO—SiN—SiO ("ONO") stack of 100-100-100 nm thickness or SiN—SiO—SiN ("NON") stack having the same thicknesses. This dielectric layer (16) is deposited on top of the barrier layer (12) by a method of plasma-enhanced chemical vapour deposition (PECVD), which is a stress-free deposition technique.

Electrical metallizations (14) connect the PC-HEMT to the electric circuit and enable electric current flow between ohmic contacts (15). The electrical metallizations (14) are made of metal stacks, such as Cr/Au, Ti/Au, Ti/W, Cr/Al and Ti/Al. The Cr or Ti layers of the metal stack is, for example, of 5-10 nm thickness, while the second metal layer, such as Au, W and Al, is of 100-400 nm thickness. The electrical metallizations are chosen according to the established technology and assembly line at a particular clean room fabrication facility. In yet further embodiment, the source and drain ohmic contacts (15) are made of metal stacks, such as Ti/Al/Mo/Au, Ti/Al/Ni/Au, Ti/Au and Ti/W having 15-50 nm thickness.

In yet further embodiment, substrate layer (10) comprises a suitable material for forming the barrier layer and is composed, for example, of sapphire, silicon, silicon carbide, gallium nitride or aluminium nitride. The hetero-junction structure (11,12) is deposited on the substrate layer (10), for example, by a method of metalorganic chemical vapour deposition (MOCVD), and forms a two-dimensional electron gas (2DEG) channel (13) in the close proximity to the interface between the buffer layer (11) and the barrier layer (12). The barrier layer (12) then may be either recessed or grown as a thin layer between the ohmic contacts (15), thereby forming an open gate area.

In a further aspect, the hetero-junction structure may be a three-layer structure consisting of two buffer layers and one barrier layer squeezed between said buffer layers like in a sandwich, wherein the top layer is a buffer layer. This may lead to formation of the two-dimensional hole gas (2DHG) in the top buffer layer above the barrier layer which results in reversing polarity of the transistor compared to the two-layer structure discussed above.

In general, polarity of III-V nitride semiconductor materials strongly affects the performance of the transistors based on these semiconductors. The quality of the wurtzite GaN materials can be varied by their polarity, because both the incorporation of impurities and the formation of defects are related to the growth mechanism, which in turn depends on surface polarity. The occurrence of the 2DEG/2DHG and the optical properties of the hetero-junction structures of nitride-based materials are influenced by the internal field effects caused by spontaneous and piezo-electric polarizations. Devices in all of the III-V nitride materials are fabricated on polar {0001} surfaces. Consequently, their characteristics depend on whether the GaN buffer layers exhibit Ga-face positive polarity or N-face negative polarity. Thus, as a result of the wurtzite GaN materials polarity, any GaN layer has two surfaces with different polarities, a Ga-polar surface and an N-polar surface. A Ga-polar surface is defined herein as a surface terminating on a layer of Ga atoms, each of which has one unoccupied bond normal to the surface. Each surface Ga atom is bonded to three N atoms in the direction away from the surface. In contrast, an N-polar surface is defined as a surface terminating on a layer of N atoms, each of which has one unoccupied bond normal to the surface. Each surface N atom is also bonded to three Ga atoms in the direction away from the surface. Thus, the N-face polarity structures have the reverse polarity to the Ga-face polarity structures.

As described above for the two-layer heterojunction structure, the barrier layer is always placed on top of the buffer layer. The layer which is therefore recessed is the barrier layer, specifically the AlGaN layer. As a result, since the 2DEG is used as the conducting channel and this conducting channel is located slightly below the barrier layer (in a thicker region of the GaN buffer layer), the hetero-junction structure is grown along the {0001}-direction or, in other words, with the Ga-face polarity. However, as explained above, the physical mechanism that leads to the formation of the 2DEG is a polarisation discontinuity at the AlGaN/GaN interface, reflected by the formation of the polarisation-induced fixed interface charges that attract free carriers to form a two-dimensional carrier gas. It is a positive polarisation charge at the AlGaN/GaN interface that attracts electrons to form 2DEG in the GaN layer slightly below this interface.

As noted above, polarity of the interface charges depends on the crystal lattice orientation of the hetero-junction structure, i.e. Ga-face versus N-face polarity, and the position of the respective AlGaN/GaN interface in the hetero-junction structure (above or below the interface). Therefore, different types of the accumulated carriers can be present in the hetero-junction structure of the embodiments.

In case of the three-layer hetero-junction structure, there are four possible configurations:

Ga-Face Polarity
1) The Ga-face polarity is characterised by the 2DEG formation in the GaN layer below the AlGaN barrier layer. This is actually the same two-layer configuration as described above, but with addition of the top GaN layer. In this configuration, the AlGaN barrier layer and two GaN buffer layers must be nominally undoped or n-type doped.
2) In another Ga-face configuration shown in FIG. 5a, in order to form the conducting channel comprising a two-dimensional hole gas (2DHG) in the top GaN layer above the AlGaN barrier layer in the configuration, the AlGaN barrier layer should be p-type doped (for example, with Mg or Be as an acceptor) and the GaN buffer layer should be also p-type doped with Mg, Be or intrinsic.

N-Face Polarity

3) The N-face polarity is characterised by the 2DEG formation in the top GaN layer above the AlGaN barrier layer, as shown in FIG. 5b. In this case, the AlGaN barrier layer and two GaN buffer layers must be nominally undoped or n-type doped.

4) The last configuration assumes that the 2DHG conducting channel is formed in the buffer GaN layer below the AlGaN barrier layer. The top GaN layer may be present (three-layer structure) or not (two-layer structure) in this case. The AlGaN barrier layer must be p-type doped (for example with Mg or Be as an acceptor) and the bottom GaN layer should be also p-type doped with Mg, Be or intrinsic.

Thus, there are four hetero-junction three-layer structures implemented in the transistor of the embodiments, based on the above configurations:

A. Ga-Face GaN/AlGaN/GaN heterostructure with the 2DEG formed in the GaN buffer layer below the AlGaN barrier layer. In this case, the top GaN layer may be omitted to obtain the two-layer structure. For the three-layer structure, the top GaN layer must be recessed to 1-9 nm thickness in the open gate area or grown with this low thickness, with the roughness below 0.2 nm, and the thickness of the AlGaN barrier can be adjusted properly during growth.

B. Ga-Face GaN/AlGaN/GaN heterostructure with the 2DHG conducting channel formed in the top GaN layer above the AlGaN barrier layer. The top GaN layer must be recessed to 5-9 nm thickness in the open gate area with the roughness below 0.2 nm, and the thickness of the AlGaN barrier layer can be adjusted properly. P-type doping concentrations of the GaN layer and AlGaN barrier have to be adjusted; the 2DHG has to be contacted (in the ideal case by ohmic contacts).

C. N-Face GaN/AlGaN/GaN heterostructure with the 2DEG in the top GaN layer above the AlGaN barrier layer. The top GaN layer must be recessed to 5-9 nm thickness in the open gate area with the roughness below 0.2 nm Thickness of the AlGaN barrier can be adjusted during growth. N-type doping levels of the GaN buffer layer and the AlGaN barrier layer must be adjusted; the 2DEG has to be contacted (in the ideal case by ohmic contacts).

N-Face GaN/AlGaN/GaN heterostructure with the 2DHG in the GaN buffer layer below the AlGaN barrier layer. In this case, the top GaN layer may be omitted to obtain the two-layer structure. In both, the two-layer and three-layer configurations, the top GaN layer must be recessed to 1-9 nm thickness in the open gate area with the roughness below 0.2 nm, and the thickness of the AlGaN barrier can be adjusted properly.

Figure 6:
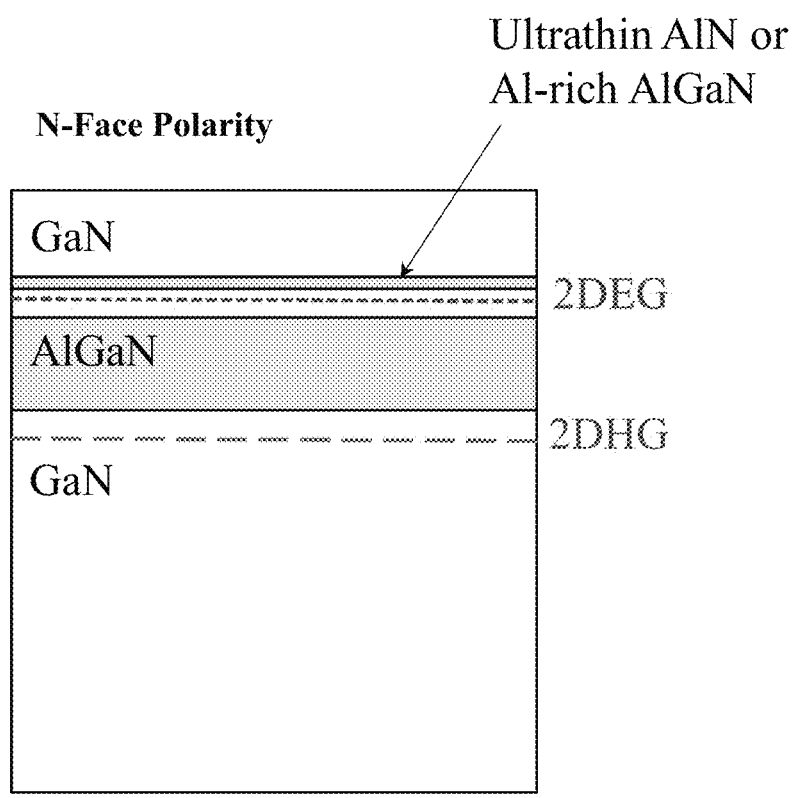
FIG. 6 schematically shows the formation of the 2DEG conducting channel in the N-face three-layer Ga/AlGaN/GaN PC-HEMT structure with an ultrathin Al(GaN)N layer for improved confinement.

In all the above structures, the deposition of a dielectric layer on top might be beneficial or even necessary to obtain a better confinement (as in case of the N-face structures). As shown in FIG. 6, for the above "C" structure, it may be even more beneficial to include an ultrathin (about 1 nm) AlN or AlGaN barrier layer with high Al-content on top of the 2DEG channel to improve the confinement.

The preferable structures of the embodiments are structures "B" and "C". In the structure "B", the 2DHG conducting channel formed in the top GaN layer, which has a higher chemical stability (particularly towards surface oxidation) than the AlGaN layer. Concerning the structure "C", the 2DEG conducting channel might be closer to the surface. Therefore, the electron mobility might be lower than in the 2DEG structure with the Ga-face polarity. In general, the polarity of the heterostructure can be adjusted by the choice of the substrate (e.g. C-face SiC) or by the growth conditions.

The 2DEG/2DHG channel (13) formed near the interface between the buffer layer (11) and the barrier layer (12) constitutes a main sensitive element of the transistor reacting to a surface charge and potential. The 2DEG/2DHG channel (13) is therefore configured to interact with very small variations in surface or proximal charge or changes of electrical field on the AlGaN barrier layer/liquid or barrier layer/metal/liquid interfaces interacting with the donor-like surface trap states of the barrier layer. This will be defined and discussed below in detail.

The term "2DEG" mentioned in the following description and claims should not be understood or interpreted as being restricted to the two-dimensional electron gas. As stated above, the two-dimensional hole gas may also be a possible current carrier in a specific hetero-junction structure. Therefore, the term "2DEG" may be equally replaced with the term "2DHG" without reference to any specific PC-HEMT configuration.

Significant features of the present PC-HEMT structure are:

(i) the AlGaN barrier layer (12) has a thickness of 5-9 nm in the open gate area (d) between the ohmic contacts (15), preferably 6-7 nm, more preferably 6.3 nm, corresponding to the pseudo-conducting current range between normally-on and normally-off operation mode of the transistor, and (ii) the surface of this barrier layer (12) within the open gate area has a roughness of 0.2 nm or less, preferably 0.1 nm or less, more preferably 0.05 nm.

"Open gate area" of the PC-HEMT is defined as an area between the source and drain ohmic contacts of the transistor which is directly exposed to a conductive medium, such as liquid or gas capable of conducting current. An example of the conductive liquid is an electrolyte saline solution. In this case, instead of the fixed gate voltage, which is normally applied to a gate electrode, a reference potential is applied to the electrolyte-semiconductor system, via an optional reference electrode that is dipped into the electrolyte. As a result, in the absence of the physical gate, the electrolyte itself becomes an open gate of the transistor. This will be explained in more detail below.

The specific thickness of the AlGaN barrier layer (12) in the open gate area is achieved by either dry etching the semiconductor material of the AlGaN layer (12), i.e. recessing the layer in the open gate area with the etching rate of 1 nm per 1-2 min in a controllable process, or coating the GaN buffer layer (11) in the open gate area with an ultrathin layer of the AlGaN microcrystalline material. In order to increase the charge sensitivity of the transistor, the surface of the recessed ultrathin barrier layer is post-treated with plasma (chloride) epi-etch process. Consequently, the natively passivated surface is activated by the plasma etch to create an uncompensated (ionised) surface energy bonds or states, which are neutralized after MOCVD growing.

In a particular embodiment, a sensor comprises the PC-HEMT of the present invention, or an array thereof, printed on a flexible printed circuit board (PCB), and each one of said PC-HEMT is connected via its ohmic contacts to its dedicated electrical contact line also printed on said PCB. Any suitable voltage source, such as Li-ion type battery, is then connected to said electrical contact lines via the electric circuit for supplying electric current to said transistors. Additional elements of the sensor installed on said PCB are complementary metal-oxide-semiconductor (CMOS) current amplifier connected to said voltage source for amplification of an electric current obtained from said transistors, an analogue-to-digital converter (ADC) with in-built digital input/output card connected to said current amplifier for outputting the converted signal to a user interface, and a connection module for remote connection of the sensor to the user interface.

All the above components of the sensor can be external or internal, i.e. built in the transistor. Each PC-HEMT of the prototype sensor of the present application is now fabricated on the substrate comprising 6-inch silicon wafers, the GaN buffer layer and the ultrathin-grown AlGaN barrier layer, as described above. The AlGaN/GaN heterojunction parameters used in this particular PC-HEMT were optimised for the AlGaN barrier layer as follows: 3.5 nm SiN cap on top of the AlGaN layer, 6 nm $Al_{0.25}Ga_{0.75}N$ and 2 µm GaN layer deposited on the Si wafer substrate. All the measurements further exemplified with this sensor were carried out on the fabricated samples without any additional surface treatment after ion implantation based 2DEG/2DHG patterning step.

Since the PC-HEMT-based sensors of the present application are very small in size and should be encapsulated within a small capsule or pill for remote operation inside the intestine or gut, they must have a very small power consumption saving the battery life for a prolong usage. In this case, the ohmic contacts of the sensor chip must be replaced with non-ohmic high-resistive contacts capacitively connecting the sensor to its electric circuit. The non-ohmic contacts replacing the ohmic contacts effectively limit an electric current flowing through the 2DEG/2DHG conducting channel by having an electrical resistance 3-4 times higher than the resistance of the 2DEG/2DHG-channel, thereby reducing electrical power consumption without sacrificing sensitivity and functionality of the sensor. Thus, the use of non-ohmic contacts in some embodiments of the sensor of the present application is a hardware solution allowing minimising the power consumption of the swallowable capsule or pill.

Figure 7A:
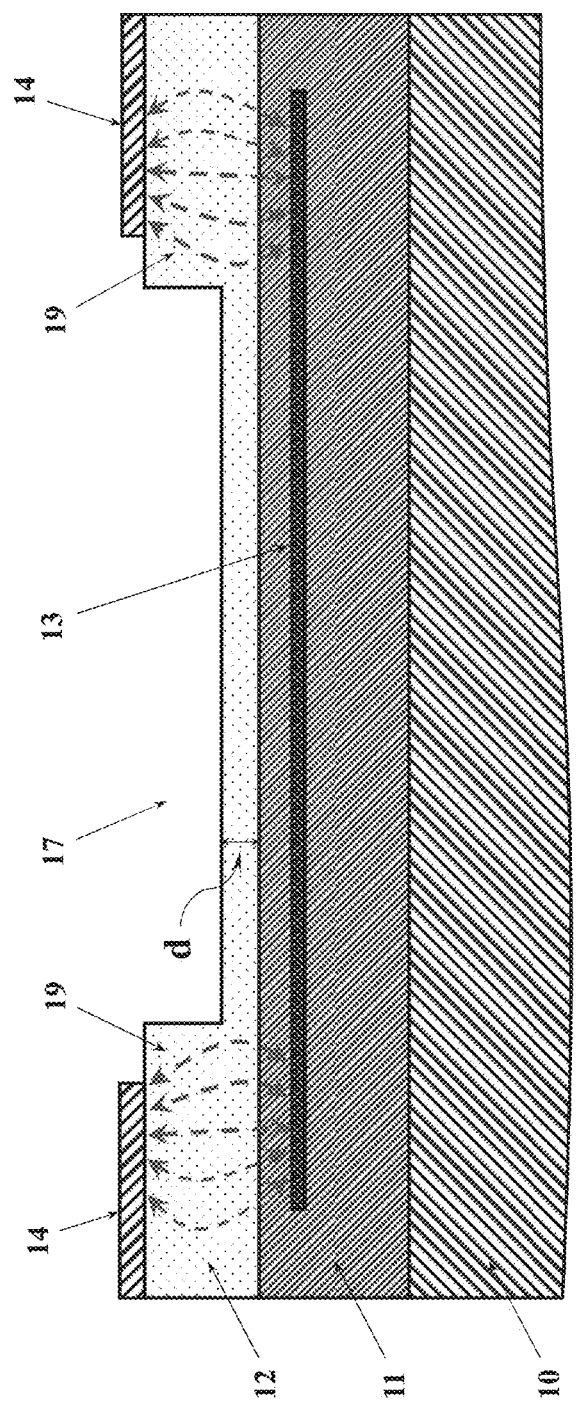
FIG. 7a schematically shows a cross-sectional view of the PC-HEMT of an embodiment with capacitively-coupled non-ohmic source and drain contacts and without a dielectric layer.

FIG. 7a shows a cross-sectional view of an open-gate pseudo-conductive high-electron mobility transistor (PC-HEMT) of an embodiment of the present application comprising:
 a multilayer heterojunction structure made of III-V single-crystalline or polycrystalline semiconductor materials, said structure comprising at least one buffer layer (11) and at least one barrier layer (12), said layers being stacked alternately, and said structure being deposited on a substrate layer (10);
 a conducting channel (13) comprising a two-dimensional electron gas (2DEG) or a two-dimensional hole gas (2DHG) formed at the interface between said at least one buffer layer (11) and said at least one barrier layer (12) and providing electron or hole current in said transistor;
 electrical metallizations (14) capacitively-coupled to said 2DEG/2DHG channel (13) for inducing displacement currents (19), thereby creating source and drain non-ohmic contacts connecting said transistor to an electric circuit; and
 an open gate area (17) between said source and drain non-ohmic contacts;
wherein:
 (i) the thickness (d) of said barrier layer (12) in said open gate area (17) is in the range of 5-9 nm, which corresponds to the pseudo-conducting current range between normally-on and normally-off operation mode of the transistor, and
 (ii) the surface of said barrier layer (12) has a roughness of about 0.2 nm or less.

Figure 7B:
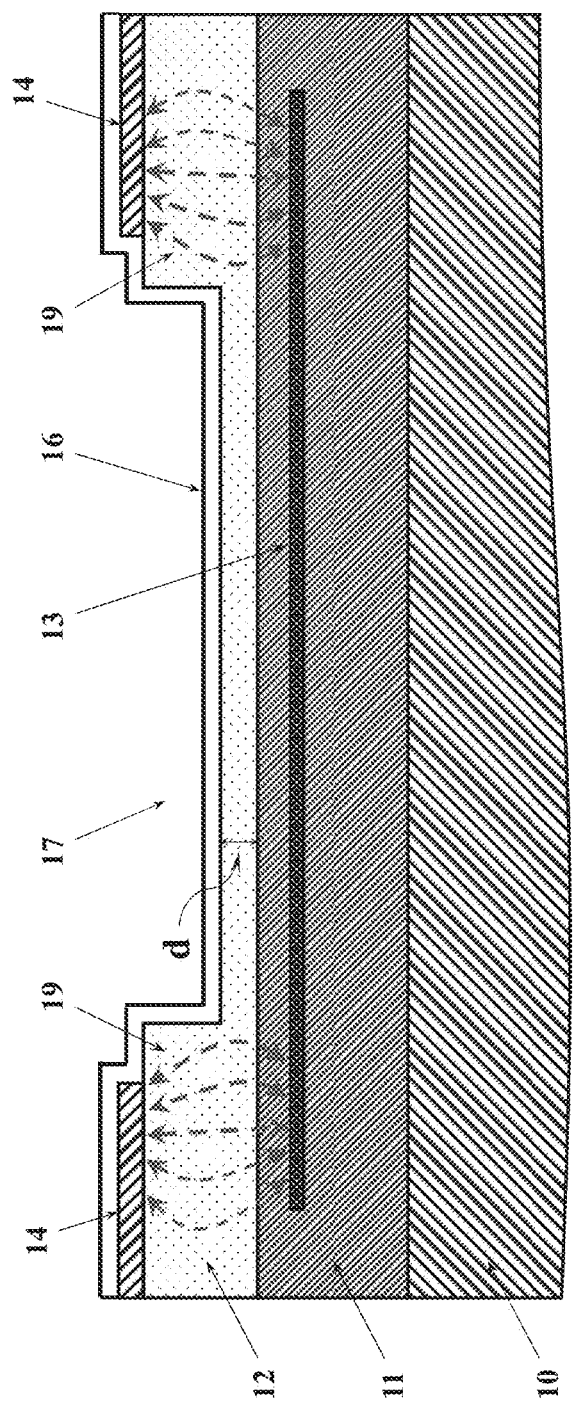
FIG. 7b schematically shows a cross-sectional view of the PC-HEMT of an embodiment with capacitively-coupled non-ohmic source and drain contacts and with a dielectric layer.

The PC-HEMT, which is shown on FIG. 7a, may further comprise a dielectric layer (16) of 1-10 nm thickness. This dielectric layer (16) is deposited on top of the barrier layer (12), as schematically shown in FIG. 7b, and has the same characteristics as the dielectric layer described above for the PC-HEMT with the ohmic contacts.

"Capacitive coupling" is defined as an energy transfer within the same electric circuit or between different electric circuits by means of displacement currents induced by existing electric fields between circuit/s nodes. In general, ohmic contacts are the contacts that follow Ohm's law, meaning that the current flowing through them is directly proportional to the voltage. Non-ohmic contacts however do not follow the same linear relationship of the Ohm's law. In other words, electric current passing through non-ohmic contacts is not linearly proportional to voltage. Instead, it gives a steep curve with an increasing gradient, since the resistance in that case increases as the electric current increases, resulting in increase of the voltage across non-ohmic contacts. This is because electrons carry more energy, and when they collide with atoms in the conductive channel, they transfer more energy creating new high-energy vibrational states, thereby increasing resistance and temperature.

When electrical metallizations are placed over microcrystalline semiconductor material, the "Schottky contact" or "Schottky barrier contact" between the metal and the semiconductor occurs. Energy of this contact is covered by the Schottky-Mott rule, which predicts the energy barrier between a metal and a semiconductor to be proportional to the difference of the metal-vacuum work function and the semiconductor-vacuum electron affinity. However, this is an ideal theoretical behaviour, while in reality most interfaces between a metal and a semiconductor follow this rule only to some degree. The boundary of a semiconductor crystal abrupt by a metal creates new electron states within its band gap. These new electron states induced by a metal and their occupation push the centre of the band gap to the Fermi level. This phenomenon of shifting the centre of the band gap to the Fermi level as a result of a metal-semiconductor contact is defined as "Fermi level pinning", which differs from one semiconductor to another. If the Fermi level is energetically far from the band edge, the Schottky contact would preferably be formed. However, if the Fermi level is close to the band edge, an ohmic contact would preferably be formed. The Schottky barrier contact is a rectifying non-ohmic contact, which in reality is almost independent of the semi-conductor or metal work functions.

Thus, a non-ohmic contact allows electric current to flow only in one direction with a non-linear current-voltage curve that looks like that of a diode. On the contrary, an ohmic contact allows electric current to flow in both directions roughly equally within normal device operation range, with an almost linear current-voltage relationship that comes close to that of a resistor (hence, "ohmic").

FIGS. 7a and 7b illustrate the situation when an electrical connection of the transistor to the 2DEG/2DHG channel is realised via capacitive coupling to electrical metallizations through a Schottky barrier contact. This coupling becomes possible only if sufficiently high AC frequency, higher than 30 kHz, is applied to the metallizations. The electrical metallizations capacitively coupled to the 2DEG channel utilise the known phenomenon of energy transfer by displacement currents. These displacement currents are induced by existing electrical fields between the electrical metallizations and the conducting channel operated in the AC frequency mode through the Schottky contact as explained above.

Figure 7C:
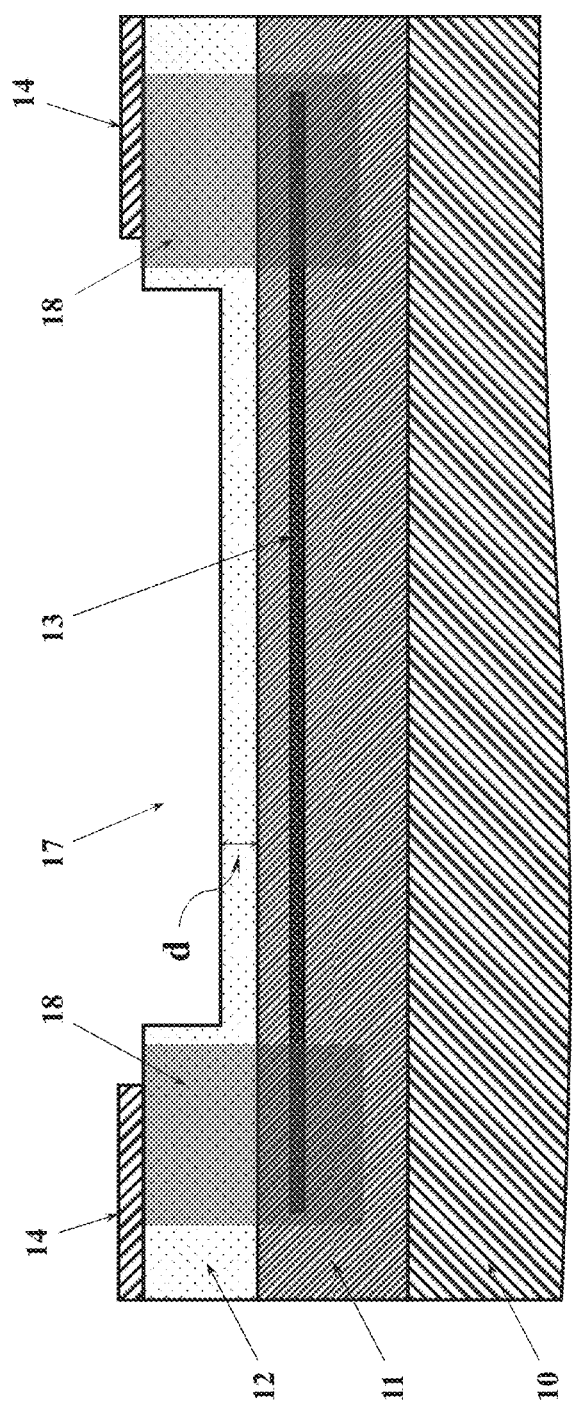
FIG. 7c schematically shows a cross-sectional view of the PC-HEMT of an embodiment with highly-doped source and drain areas.

Reference is now made to FIG. 7c schematically showing a cross-sectional view of the PC-HEMT of an embodiment of the present application with highly-doped source and drain areas (18). In this case, the strong doping of the source and drain areas may result in a band-edge mismatch. However, if the semiconductor is doped strongly enough, it will form a potential barrier low enough for conducting electrons to have a high probability of tunnelling through, thereby conducting an electric current through the conducting 2DEG channel.

An electrical connection to the 2DEG channel shown in FIG. 7c is realised with a highly doped semiconductor areas (18) overlapping the 2DEG channel and having a very low electrical resistance. Dopant ions such as boron ($B^+$), phosphorus ($P^+$) or arsenic ($As^+$) are generally created from a gas source, so that the purity of the source can be very high. When implanted in a semiconductor, each dopant atom creates a charge carrier in the semiconductor material after annealing. Holes are created for a p-type dopant, and electrons are created for an n-type dopant, modifying conductivity of the semiconductor in its vicinity. $As^+$ can be used for n-type doping, while $B^+$ and $B^+$ ions can be used for p-type doping. For example, in case of the AlGaN/GaN structure, the source and drain areas of the silicon structure are heavily doped with either $B^+$ or $B^+$ to create an electrical connection to the 2DEG channel. The silicon layers have a very low electrical junction resistance between each other in that case, and in order to induce an electrical current in the 2DEG channel, the metallizations are placed on top of the source and drain areas and connected to a circuit.

The third option of minimising the power consumption of the sensor would be the use of the photoeffect that may also induce an electric current in the 2DEG channel. In order to couple the light excitation with the electronic effects in the 2DEG channel, the photoeffect in a silicon layer should be created. Regarding the direct photoeffect, it is well known that light can only be absorbed when the energy of the absorbed photon, defined as $E=h\nu$, is large enough for an electron to be excited into the valence band. In that case, h is Planck's constant and $\nu$ is the frequency of the photon. The frequency is coupled to the wavelength $\lambda$ of light by the constant speed of light $c=4$. Typically the bandgap of silicon at room temperature is 1.12. eV, which means that silicon becomes transparent for wavelength larger than 1240 nm, which is the near infrared range.

For smaller wavelength (i.e. larger energy of the photons), electron/hole pairs are generated leading to a photocurrent. In the fully-depleted, intrinsically doped silicon structures, this results in a higher charge carrier density and consequently, higher sensitivity. For these structures, light is adsorbed in the whole visible range making such devices ideal photodetectors. The mechanism that allows the silicon semiconductor to become photosensitive to irradiation with light has already been described in literature. In the direct photoeffect, it can be tuned by the size, crystalline direction and surface termination. These effects originate from two-dimensional quantum confinement of electrons in the nano-sized 2DEG structure.

Although irradiation of the silicon structure with light of larger wavelengths with photon energies below the bandgap does not have enough energy to excite carriers from the valence to the conduction band in bulk silicon, the electron/hole pairs can also be generated between the valence band and surface states, and the donor-like surface trap states can still be formed (see the definition and explanation of the surface trap states below). The electrons actually deplete the holes trapped at the surface and hence, modulate the gate field. The photogenerated holes are confined to the centre of the silicon structure by the gate field, where they increase the conduction of the 2DEG channel, because of the band bending. The holes increase the channel conductivity for a certain lifetime until they are trapped (recaptured) at the surface. The gain of the transistor can be extremely huge if this re-trapping lifetime is much longer than the holes transit time.

The above described PC-HEMT configurations may optionally include an electro-optical (EO) crystalline material, such as lithium niobate ($LiNbO_3$) or lithium tantalite ($LiTaO_3$). The excitation light beam irradiates the EO crystals with a polarised light of 400-600 nm wavelength range, followed by irradiating the PC-HEMT-based sensor. As explained above, the PC-HEMT is also ultrasensitive to the excitation light creating the p-n-pairs in the AlGaN layer and strongly affecting the 2DEG conductivity. In the ultrasensitive state of the PC-HEMT, a very small number of photons can switch the 2DEG channel from a normally-off mode to a normally-on mode resulting in a strong pseudo-conducting behaviour of the PC-HEMT, which increases the sensitivity of the transistor at least three orders of magnitude.

By contact with an electrical body charge, the EO crystal changes its light absorbance. The ultrasensitive PC-HEMT is therefore able to resolve the smallest intensity changes of the excitation light transferred through the EO crystal. Because the signals recorded by the PC-HEMT from the fluid environment of the intestine and gut are relatively slow, this transistor is able to sense and record all the dynamics of these organs. Thus, using the PC-HEMT of an embodiment with the integrated EO crystal makes it possible to fully decouple the PC-HEMT from any parasitic electrical charges originated from the human body. Depending on the light wavelength, the position of the sensor relative to the incident light beam is changed. In case of the IR light, which has the wavelength range of about 700-1500 nm, the sensor should be installed inside the capsule perpendicularly to the light beam transmitted from the light source installed in the same capsule, for achieving the highest sensitivity. The parasitic charging of the EO crystal is to be compensated via electrodes attached to the crystal. Additionally, the transistor may be combined with a variety of light filters to achieve a particular wavelength of excitation.

Since the source and drain contacts are non-ohmic (capacitively-coupled), in order to electrically contact the 2DEG channel, which is formed about 5-20 nm beneath the metallizations, the AC frequency regime should be used. As mentioned above, the capacitive coupling of the non-ohmic metal contacts with the 2DEG channel is normally induced at the frequency higher than 30 kHz. In this case, the DC readout cannot be performed. Instead, the AC readout or impedance measurements of the electric current flowing through the conducting 2DEG channel are carried out.

In a further embodiment, the power consumption of the device can also be minimised using a software algorithm managing the necessary recording time of the sensor and a battery saver mode, which limits the background data and switches the wireless connection only when it is needed.

The PC-HEMT-based sensors of the invention described above are capable of diagnosing the intestine and gut conditions by sensing only the charge distribution in the liquid environment around the capsule. These sensors can therefore be defined as "charge sensitive sensors". Their sensing mechanism is explained below.

Figure 8A:
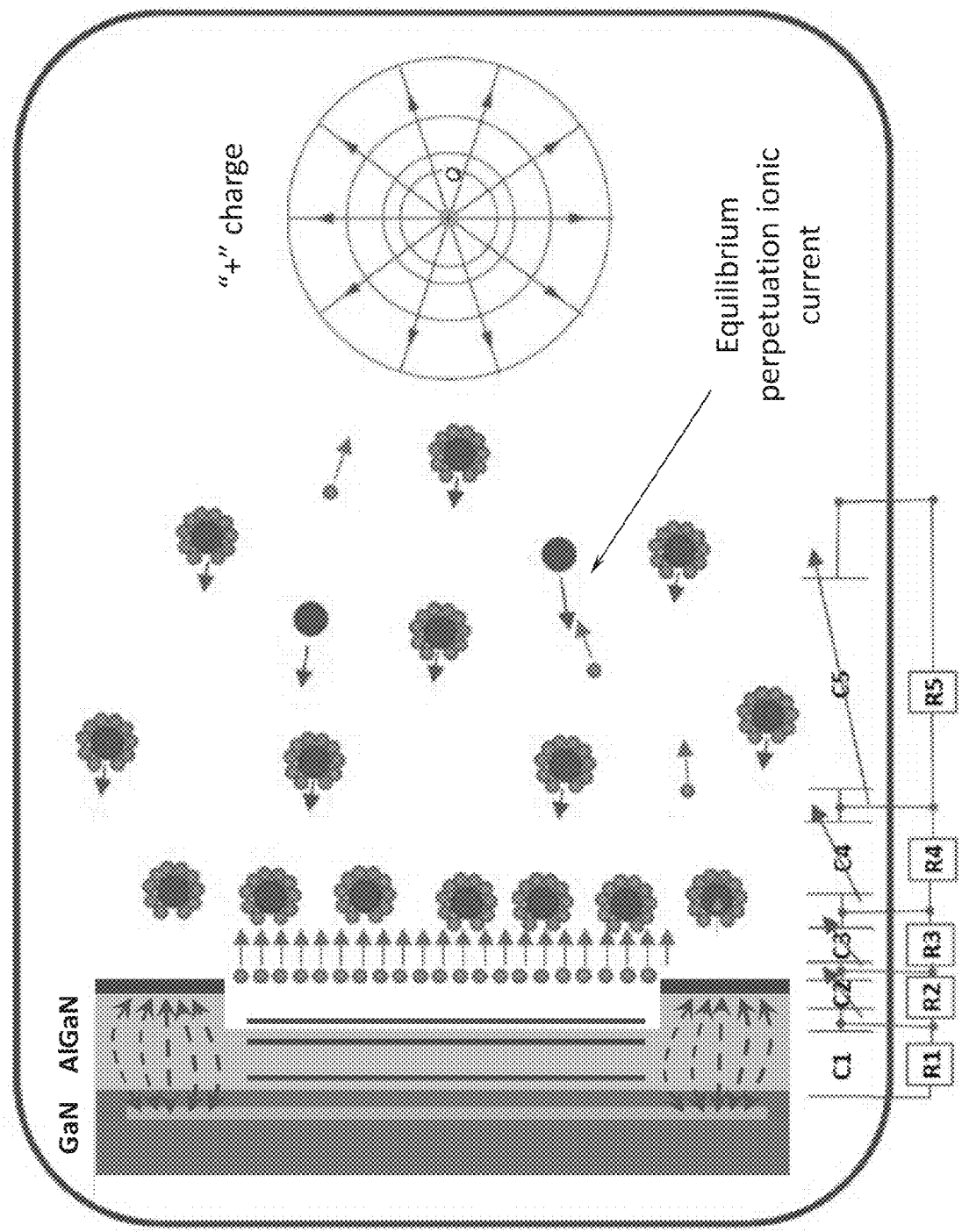
FIG. 8a schematically shows the AlGaN barrier layer/liquid interface with the double layer formation, simplified equivalent interface circuitry and ion electrodynamics during exposure of the sensor of an embodiment to a positive charge.
Figure 8B:
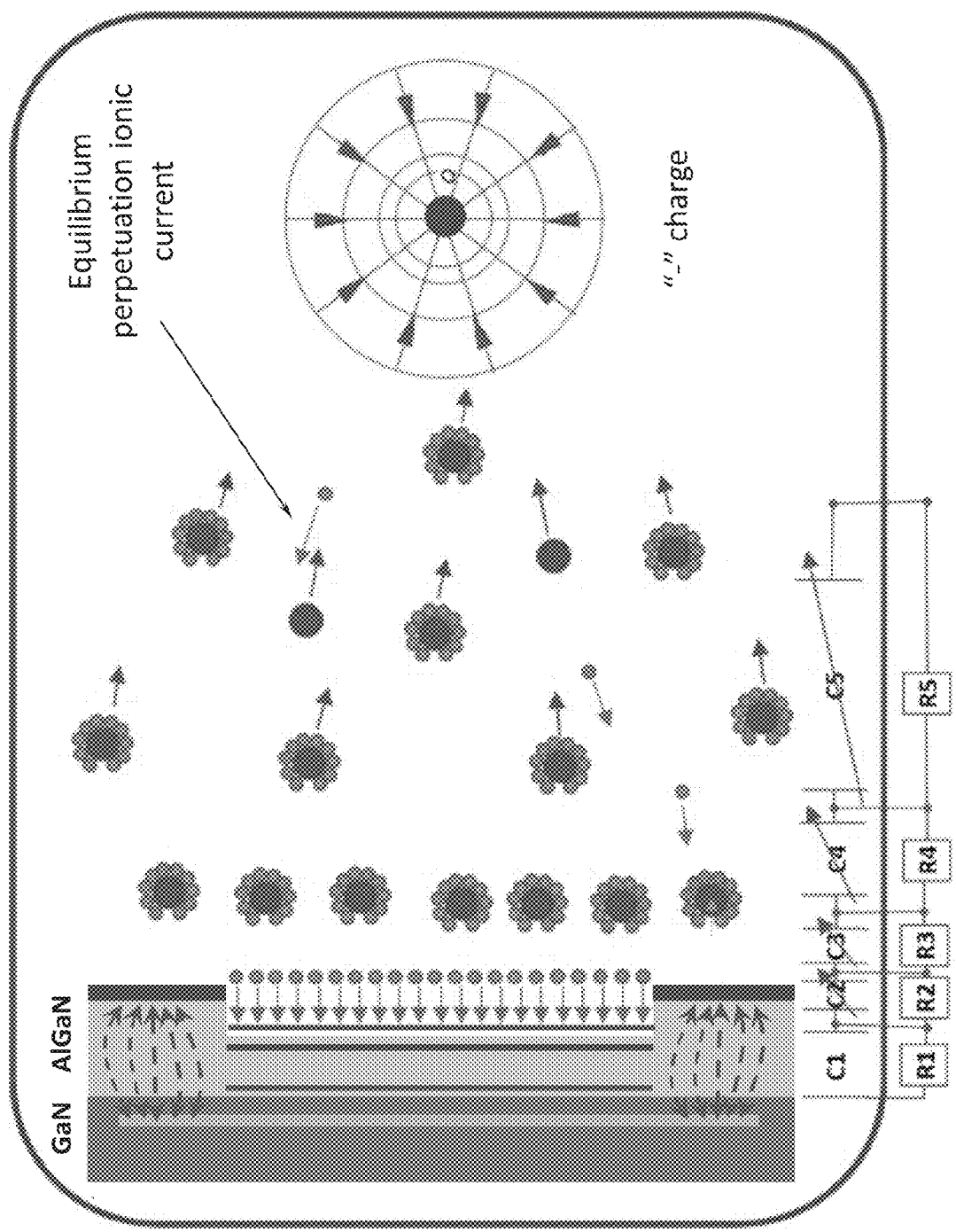
FIG. 8b schematically shows the AlGaN barrier layer/liquid interface with the double layer formation, simplified equivalent interface circuitry and ion electrodynamics during exposure of the sensor to a negative charge.

FIGS. 8a-8b schematically show the AlGaN barrier layer/liquid interface with the double layer formation, simplified equivalent interface circuitry and ion electro-dynamics during exposure of the sensor to a positive charge (FIG. 8a) and a negative charge (FIG. 8b). Placed into a liquid, any surface potential causes the natural formation of an electrochemical double layer at the contact interface to maintain charge equilibrium between the solid state and ionic conductive liquid. In FIGS. 8a and 8b, this double layer is shown schematically together with the simplified equivalent circuitry at the interface. The double layer is mostly created with a 1-3 nm thick sharp separation between the negative and positive ion space charge zones C2-R2 and C3-R3, which cause a secondary space charge equilibrium zone C4-R4 (10 nm to 1 μm) and charge gradient zone C5-R5 disappearing in the bulk liquid. When there is no more potential shift from the solid and from the liquid, then the charge equilibrium is maintained with C1/R1-C5/R5 elements possessing a quasi-constant values.

Ion flow is schematically shown in FIGS. 8a and 8b with vector arrows during an electrodynamic rearrangement when an external charge is introduced into an equilibrated electrolyte. FIG. 8a shows the electrodynamic rearrangement with an external positive charge, and FIG. 8b illustrates the electrodynamic rearrangement but with an external negative charge. When the ions react to an external electric field applied in the liquid, the equivalent circuitry mirroring the space charges changes accordingly. Since the sensor of the invention based on the PC-HEMT is extremely sensitive to any surface charge changes (C1/R1), the gradient ions rearrangement in the space charge zones from C5/R5 to a C2/R2 is able to modulate the 2DEG conductivity. The dynamic and magnitude of the new equilibrium is directly proportional to the liquid electrolyte conductivity, ions mobility and external charge value defining the resulted electrolyte charge. In general, any electrolyte strongly enhances the sensor charge response due to the excellent direct charge transfer towards the barrier layer/electrolyte interface. The ions of the intestine and gut liquid interact directly with the highly sensitive surface trap states of the ultrathin barrier layer.

Thus, when a capsule containing the PC-HEMT-based "charge-sensitive sensors" is swallowed and enter an ion-conductive liquid of an intestine and gut, the liquid ions start electro-dynamically reacting to any external charge by their movement. Being in direct contact to the AlGaN barrier layer surface, the charge sensitivity is thus tremendously enhanced. The intestine and gut liquid functions act in this case as a virtual liquid antenna perfectly matching the 2DEG transducer. These organs generate electric charges, and a super-position dipole of them is projected to a liquid antenna in which the encapsulated sensor is immersed in. Since the capsule is in a physical contact with the intestine and gut liquid, the detected signal is drastically increased, because the electric field within the intestine and gut is transferred to the liquid with minimal loses.

As discussed above, at any solid state/electrolyte interface, the capacitive and resistive elements of the sensor form an electrochemical surface potential originated from an interaction between the surface trap states and a double layer capacity, while the interaction between the 2DEG and the surface trap states originates from tunnelling and electrostatics. It has now been surprisingly found that operation of the PC-HEMT sensor as an open gate field-effect transistor is not required in order to modulate the surface electrochemical potential within the AlGaN barrier layer/liquid electrolyte system.

The second type of the PC-HEMT-based sensors integrated inside the capsule or pill of an embodiment is "pressure-sensitive sensors", which are capable of measuring the gut pressure. These sensors use the free-standing membranes for creating a mass-loading effect. FIG. 9a shows a cross-sectional view of the PC-HEMT configuration of an embodiment with free-standing membranes, comprising:

a multilayer heterojunction structure made of III-V single-crystalline or polycrystalline semiconductor materials, said structure comprising at least one buffer layer (11) and at least one barrier layer (12), said layers being stacked alternately, and said structure being placed on free-standing membranes (23);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain contacts;

electrical metallizations (14) capacitively-coupled to said 2DEG or 2DHG conducting channel (13) for inducing displacement currents (19), thereby creating source and drain non-ohmic contacts connecting said transistor to an electric circuit; and an open gate area (17) between said source and drain non-ohmic contacts;

wherein:

(i) the thickness (d) of said barrier layer (12) between said source and drain non-ohmic contacts is about 5-9 nm which corresponds to the pseudo-conducting current range between normally-on and normally-off operation mode of the transistor; and (ii) the surface of said barrier layer (12) has a roughness of about 0.2 nm or less.

Using the above configuration with the free-standing membranes makes it possible to increase selectivity of the sensor via adding mechanical stress (mass-loading effect) as an additional parameter of the PC-HEMT-based sensor. The free-standing membranes (23) are very flexible free-standing columns of substrate composed of sapphire, silicon, silicon carbide, gallium nitride or aluminium nitride, preferably gallium nitride, having thickness of 0.5-2 μm. The free-standing substrate membranes are very sensitive to any tensile/compressive/mechanical stress changes on the surface of the multilayer heterojunction structure. This results in a mass loading effect, which will be discussed below.

In general, mechanical sensors, much like pressure sensors, are based on the measurement of the externally induced strain in the heterostructures. The pyroelectric properties of group-III-nitrides, such as gallium nitride, allow two mechanisms for strain transduction: piezoelectric and piezoresistive. The direct piezoelectric effect is used for dynamical pressure sensing. For measuring static pressure, such sensors are not suited due to leakage of electric charges under the constant conditions. For static operation, the piezoresistive transduction is more preferable.

Piezoresistive sensors using wide band gap materials have been previously employed using hexagonal silicon carbide bulk materials for high temperature operation. Piezoresistivity of GaN and AlGaN structures is comparable to silicon carbide; however it can be further amplified by a HEMT structure, as taught by Eickhoff et al (2001). For piezoresistive strain sensing at relatively lower pressures (or pressure differences), diaphragm or membranes should be used, where the external pressure is transferred into a changed internal strain caused by bending, as shown in FIG. 9b. The resulting change in polarization alters the 2DEG channel current which is measured.

Eickhoff et al (2001) conducted the first experiments on AlGaN/GaN heterostructures where the 2DEG channel confined between the upper GaN and AlGaN barrier layer and demonstrated the linear dependence of the 2DEG channel resistivity on the applied strain. Moreover a direct comparison to cubic SiC and a single AlGaN layer clearly demonstrated the superior piezoresistive properties of the latter. From these results, it is clear that the interaction of piezoelectric and piezoresistive properties improves the sensitivity of pressure sensors by using GaN/AlGaN heterostructures confined with the 2DEG channel.

The sensor configuration schematically shown in FIGS. 9a and 9b involves piezoelectrically coupled, charge and mass sensitive, free-standing GaN membranes, which are prepared, for example, according to U.S. Pat. No. 8,313,968, and offer an elegant and effective solution to achieve both downscaling and an integrated all-electrical low-power sensing-actuation. As mentioned above, GaN exhibits both, piezo- and pyro-electrical properties, which can be functionally combined. Whereas the piezoelectricity enables realisation of an integrated coupling mechanism, the 2DEG additionally delivers a pronounced sensitivity to mechanical stress and charge, which allows the sensor to use the pyroelectric effects. The dynamic change in 2DEG conductivity is also caused by a change in piezoelectric polarisation.

FIG. 10a schematically shows a design of the autonomous capsule or pill for in-vivo sensing of an intestine and gut. As detailed above, there are two major types of the sensors based on the PC-HEMT of an embodiment installed within this capsule or pill: charge-sensitive sensor (21) and pressure-sensitive sensor (22). In addition, the combined charge-pressure sensitive sensor can be installed within the capsule for enhanced operation. As shown in FIG. 10a, these PC-HEMT-based sensors are integrated in an array together with light sources (23, 24), such as light-emitting diodes (LEDs), for neuronal activity stimulation. Thus, in a particular aspect of the present application, the swallowable capsule for intestinal and gut diagnostics comprises the following components:

a "charge-sensitive" PC-HEMT (21) of an embodiment (shown in FIGS. 5a-5c and 7a-7c), or an array thereof, installed on a flexible printed circuit board (PCB) for detecting gut tissue potentials created from neuronal signalling or from muscular peristaltic tissue potentials, wherein each one of said PC-HEMTs is connected to a microcontroller (25) via its dedicated electrical contact line printed on said PCB; at least one pair of light sources (23, 24) installed on said PCB for irradiating the surrounding tissues of an intestine and gut with two different wavelengths of light, thereby stimulating the neuronal activity of tissue cells, which is sensed by said "charge-sensitive" PC-HEMTs (21);

a "pressure-sensitive" PC-HEMT (22) of an embodiment (shown in FIG. 9a), or an array thereof, installed on a flexible printed circuit board (PCB) for detecting changes in gut pressure, wherein each one of said PC-HEMTs is connected to a microcontroller (25) via its dedicated electrical contact line printed on said PCB;

the microcontroller (25) with a digital-to-analogue (DAC) and analogue-to-digital (ADC) converter for recording and processing the signals received from said "charge-sensitive" and "pressure-sensitive" PC-HEMTs (21, 22);

a battery unit (26) connected to said electrical contact lines via an electric circuit for supplying electric current to the components of said swallowable capsule; and a cylindrically-shaped and light transparent housing for wrapping said components of said swallowable capsule up, wherein said housing is made of an ion-permeable biocompatible membrane (20).

Figure 10B:
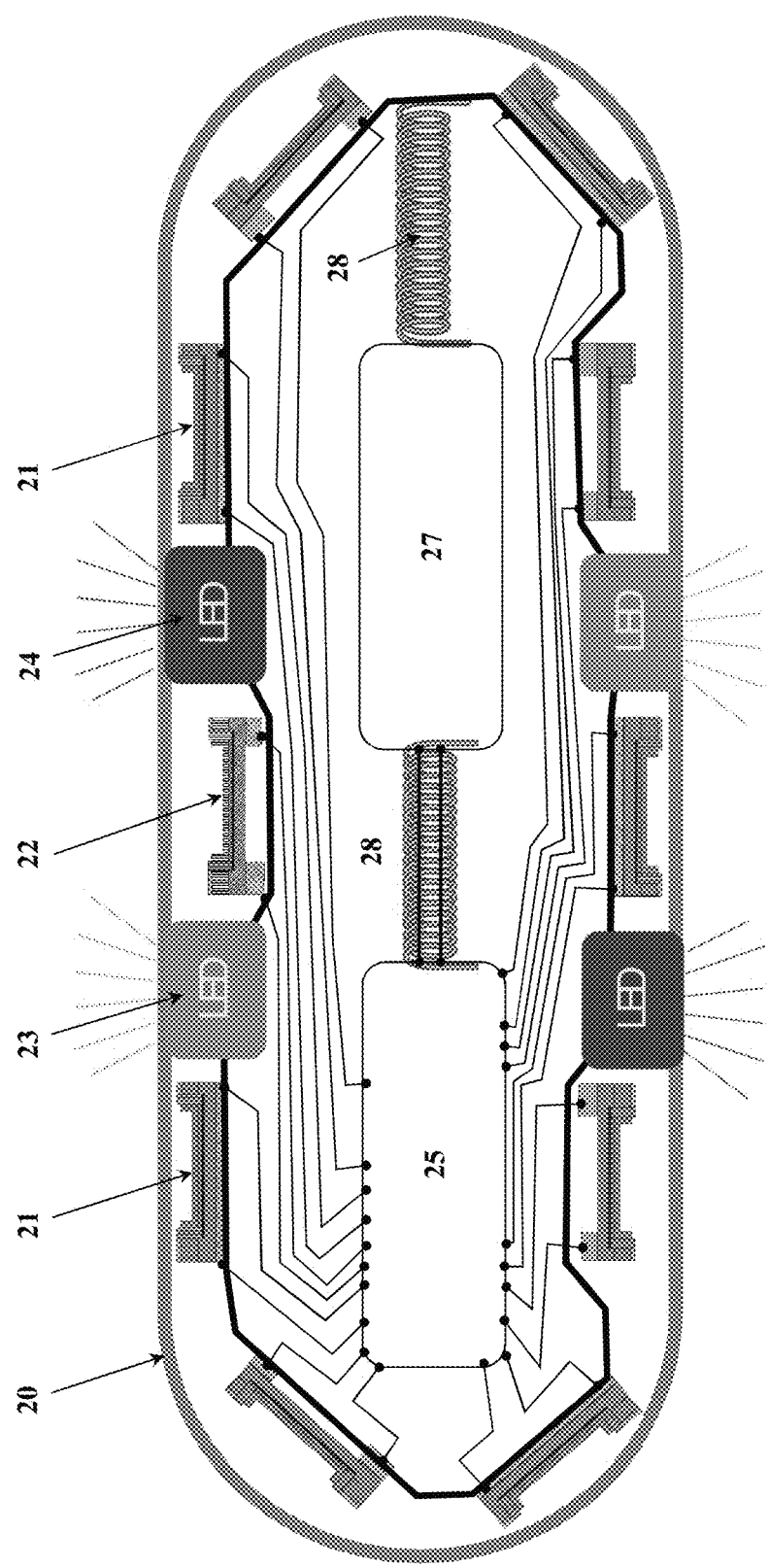
FIG. 10b schematically shows a design of the autonomous capsule with a zero-power digital near-field communication (NFC) module for in-vivo sensing of an intestine and gut.

In a further particular embodiment, the swallowable capsule for intestinal and gut diagnostics, as shown in FIG. 10b, comprises the following components:

a "charge-sensitive" PC-HEMT (21) of an embodiment (shown in FIGS. 5a-5c and 7a-7c), or an array thereof, installed on a flexible printed circuit board (PCB) for detecting gut tissue potentials created from neuronal signalling or from muscular peristaltic tissue potentials, wherein each one of said PC-HEMTs is connected to a digital-to-analogue (DAC) converter (25) via its dedicated electrical contact line printed on said PCB;

at least one pair of light sources (23, 24) installed on said PCB for irradiating the surrounding tissues of an intestine and gut with two different wavelengths of light, thereby stimulating the neuronal activity of tissue cells, which is sensed by said "charge-sensitive" PC-HEMTs (21);

a "pressure-sensitive" PC-HEMT (22) of an embodiment (shown in FIG. 9a), or an array thereof, installed on a flexible printed circuit board (PCB) for detecting changes in gut pressure, wherein each one of said PC-HEMTs is connected to a digital-to-analogue (DAC) converter (25) via its dedicated electrical contact line printed on said PCB;

a digital-to-analogue (DAC) converter (25) for converting the AC signals received from said "charge-sensitive" and "pressure-sensitive" PC-HEMTs (21, 22) to the DC signals;

an analogue-to-digital (ADC) converter (27) for processing the analogue signals received from the DAC converter (25) and converting said analogue signals to the digital signals for transmitting said digital signals to a receiver unit;

at least one pair of antennas (28) for wirelessly transmitting said digitals signals to said receiver unit; and a cylindrically-shaped and light transparent housing for wrapping said components of said swallowable capsule up, wherein said housing is made of an ion-permeable biocompatible membrane (20).

Figure 10C:
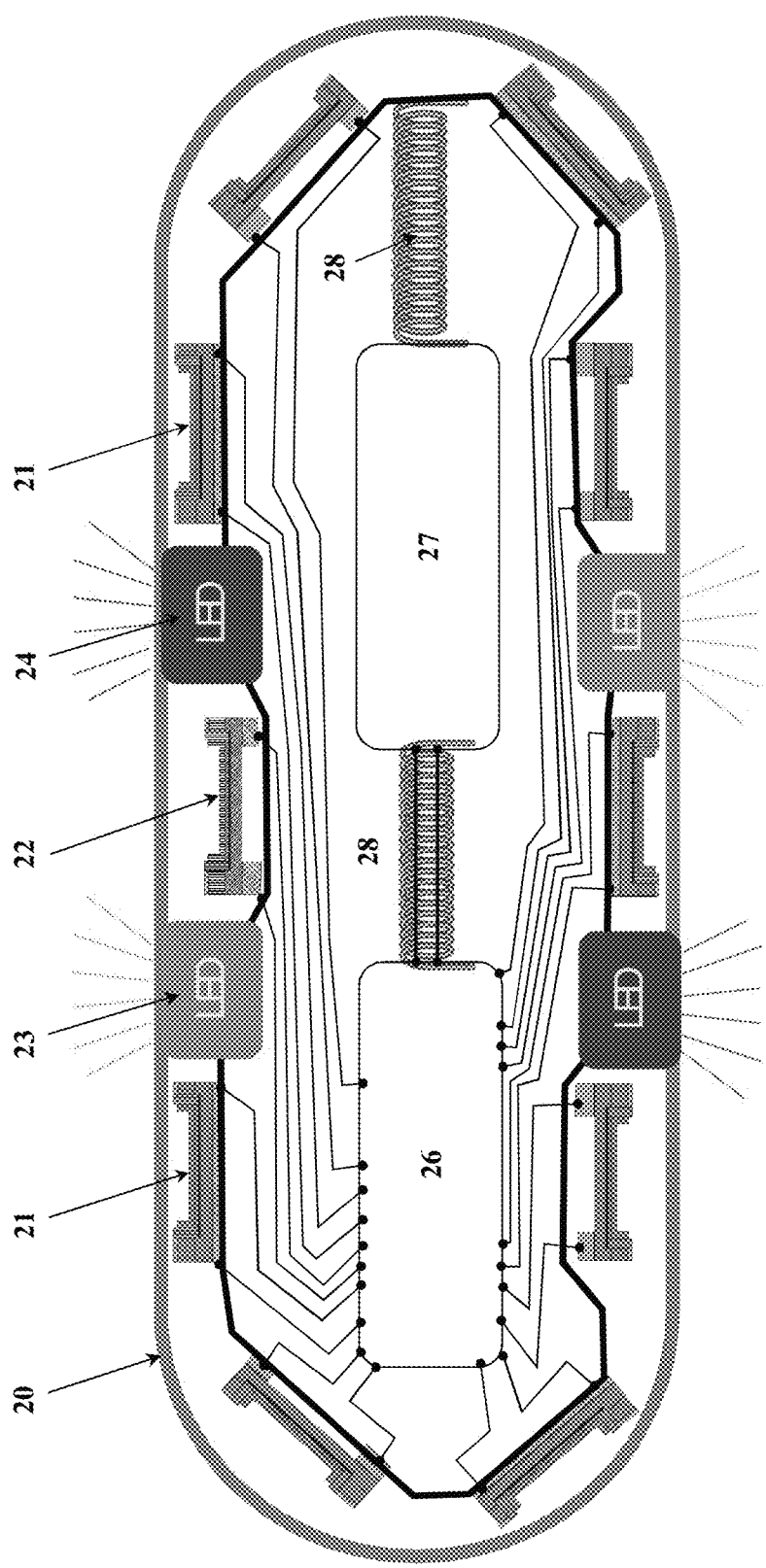
FIG. 10c schematically shows a design of the autonomous capsule with a battery-powered digital near-field communication (NFC) module for in-vivo sensing of an intestine and gut.

Thus, the DAC converter (25) together with the ADC converter (27) and at least two antennas (28) in the above configuration constitute a digital NFC zero-power module. In yet further embodiment, the swallowable capsule shown in FIG. 10c, for intestinal and gut diagnostics, comprises the following components:

a "charge-sensitive" PC-HEMT (21) of an embodiment (shown in FIGS. 5a-5c and 7a-7c), or an array thereof, installed on a flexible printed circuit board (PCB) for detecting gut tissue potentials created from neuronal signalling or from muscular peristaltic tissue potentials, wherein each one of said PC-HEMTs is powered by a battery (26) via its dedicated electrical contact line printed on said PCB;

at least one pair of light sources (23, 24) installed on said PCB for irradiating the surrounding tissues of an intestine and gut with two different wavelengths of light, thereby stimulating the neuronal activity of tissue cells, which is sensed by said "charge-sensitive" PC-HEMTs (21);

a "pressure-sensitive" PC-HEMT (22) of an embodiment (shown in FIG. 9a), or an array thereof, installed on a flexible printed circuit board (PCB) for detecting changes in gut pressure, wherein each one of said PC-HEMTs is powered by a battery (26) via its dedicated electrical contact line printed on said PCB;

a battery unit (26) connected to said electrical contact lines via an electric circuit for supplying electric current to the components of said swallowable capsule;

an analogue-to-digital (ADC) converter (27) for processing the analogue signals received by said capsule and converting said analogue signals to the digital signals for transmitting said digital signals to a receiver unit;

at least one pair of antennas (28) for wirelessly transmitting said digitals signals to said receiver unit; and a cylindrically-shaped and light transparent housing for wrapping said components of said swallowable capsule up, wherein said housing is made of an ion-permeable biocompatible membrane (20).

The above capsule configuration essentially constitutes a battery-powered digital NFC wireless configuration of the capsule of an embodiment. Thus, in all three above configurations, the coded digital signal is used to wake-up the capsule initiating the data transfer, which is recorded internally and/or as a real-time data. The current modulations inside the PC-HEMTs are transferred into a digital code by the ADC and further sent to a receiver unit, such as a smartphone, a cardphone, smartwatch or any other similar NFC-enabled device. The receiver unit may also be a desktop computer, server, remote storage, internet storage or telemedicine cloud.

In a specific embodiment, the charge-sensitive PC-HEMTs (21) may either be exposed to the liquid surroundings (have an open contact with the intestine or gut liquid), or may be covered with the thin ion-permeable biocompatible membrane (20).

Figure 11:
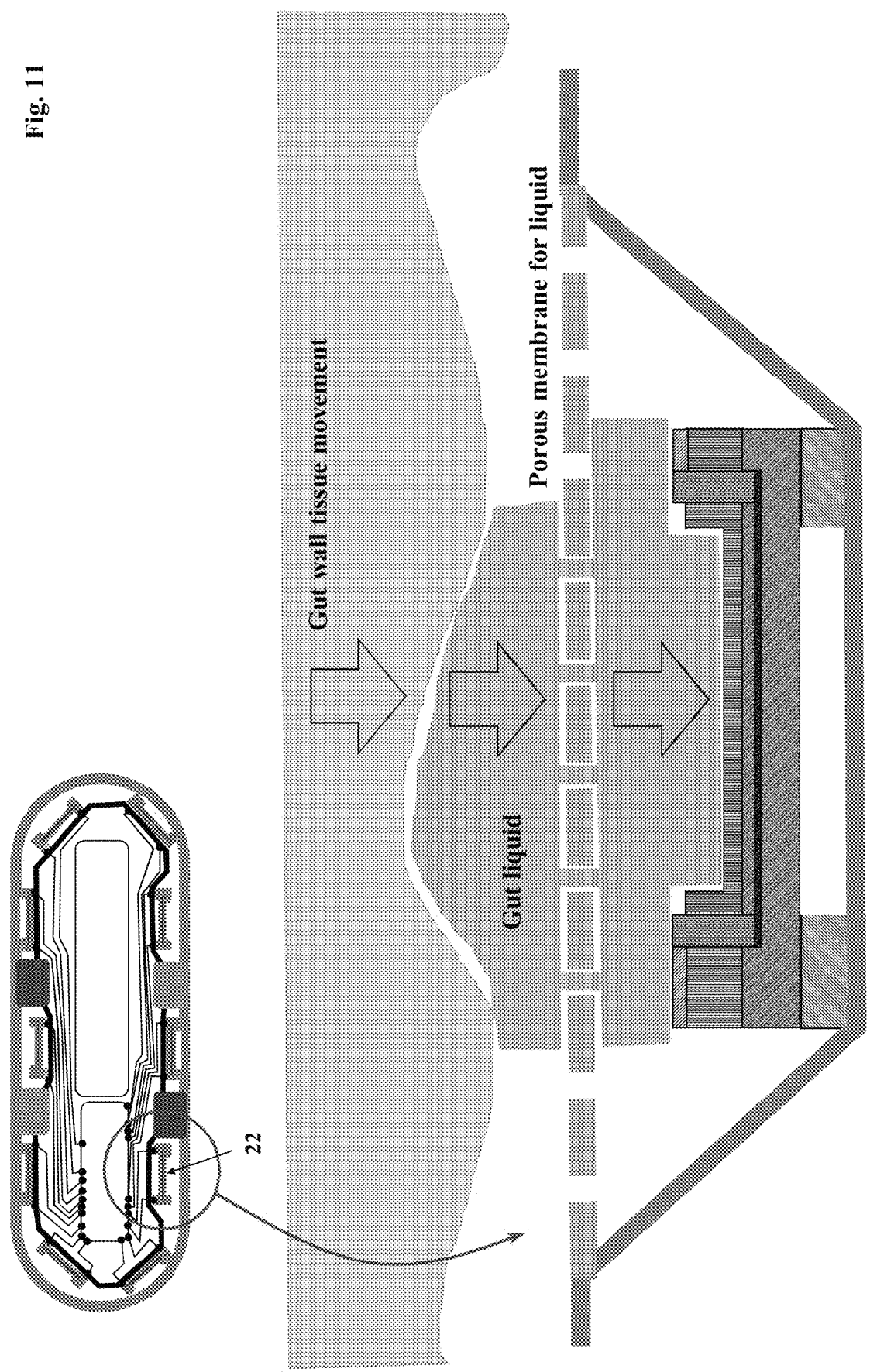
FIG. 11 illustrates how the pressure-sensitive PC-HEMTs installed within the capsule of an embodiment react to any physical movement of the gut tissue causing small local μ-variations of the liquid pressure (in the range of only few pascals).

The pressure-sensitive PC-HEMTs (22) built on the free-standing membranes are protected with a porous membrane cap placed inside the cavity of the transistor. As schematically shown in FIG. 11, the pressure-sensitive or the charge-pressure-sensitive PC-HEMTs with the free-standing membranes react to any physical movement of the gut tissue causing small local μ-variations of the liquid pressure (in the range of only few pascals). Due to the phenomenal ultrahigh pressure sensitivity of the pyroelectric free-standing membrane of these PC-HEMTs, such small changes can be resolved in case of the fast sensing mode of about 1 frames per second (fps). In that case, the pressure gradient, which rapidly changes along the gut, will be recorded.

Figure 12:
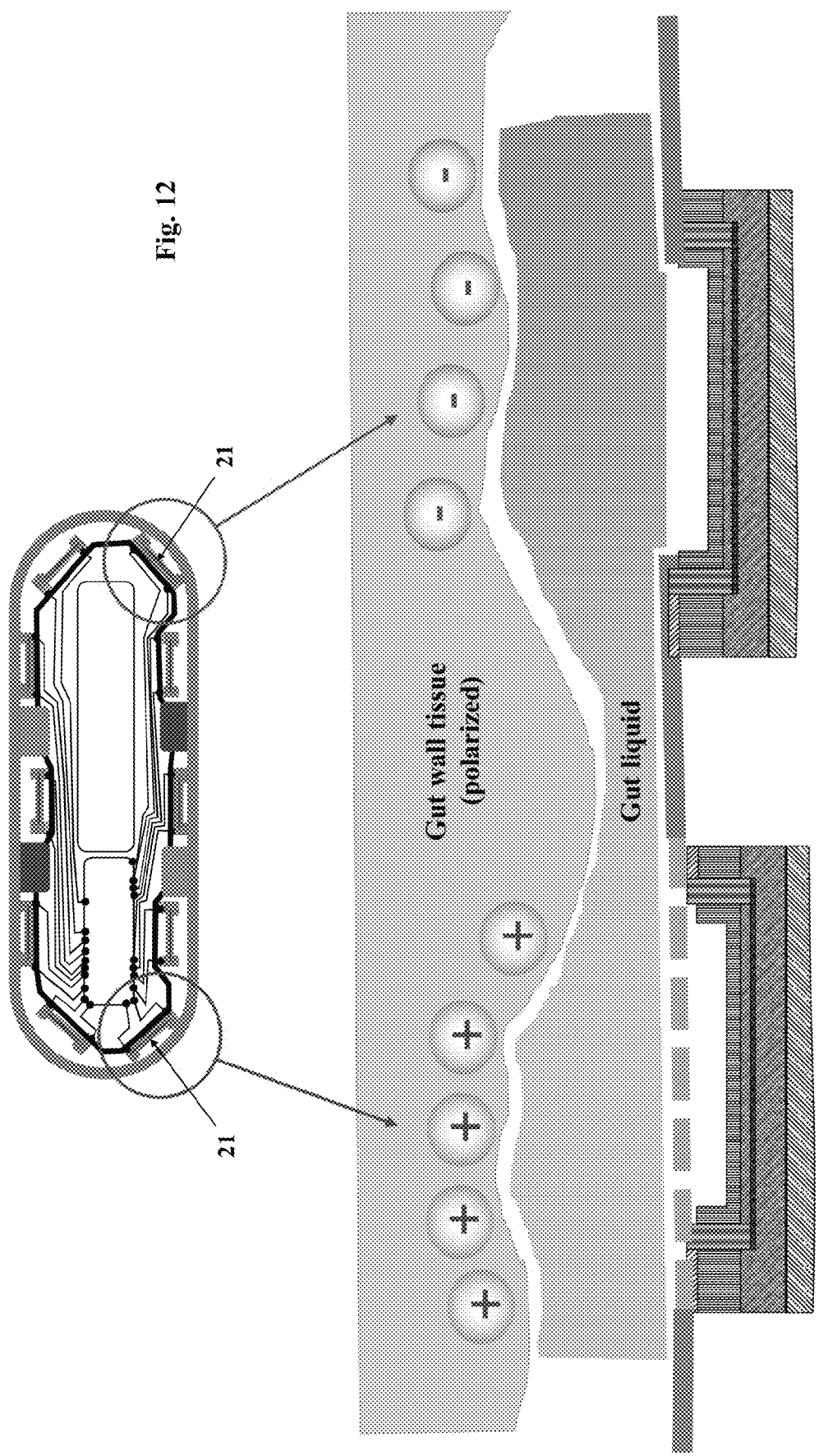
FIG. 12 illustrates the action of the charge-sensitive PC-HEMTs detecting tiniest changes in gut tissue potentials created from neuronal signalling or muscular peristaltic tissue movements.

Reference is now made to FIG. 12 schematically explaining the action of the charge-sensitive PC-HEMTs (21). Because they are mechanically much more robust and fully biocompatible, there is no extra protection necessary and they can be exposed to the intestine and gut liquid. These PC-HEMTs (21) are detecting tiniest changes in gut tissue potentials created from neuronal signalling or muscular peristaltic tissue movements. As shown in FIG. 12, the gut wall tissues are polarised though the local neuronal signalling or muscular peristaltic. As a result, despite their single point charge sensing ability, these charge-sensitive PC-HEMTs are also capable of detecting differential signals, provided that the potential differences between any of these two PC-HEMTs are measured within the capsule.

Figure 13:
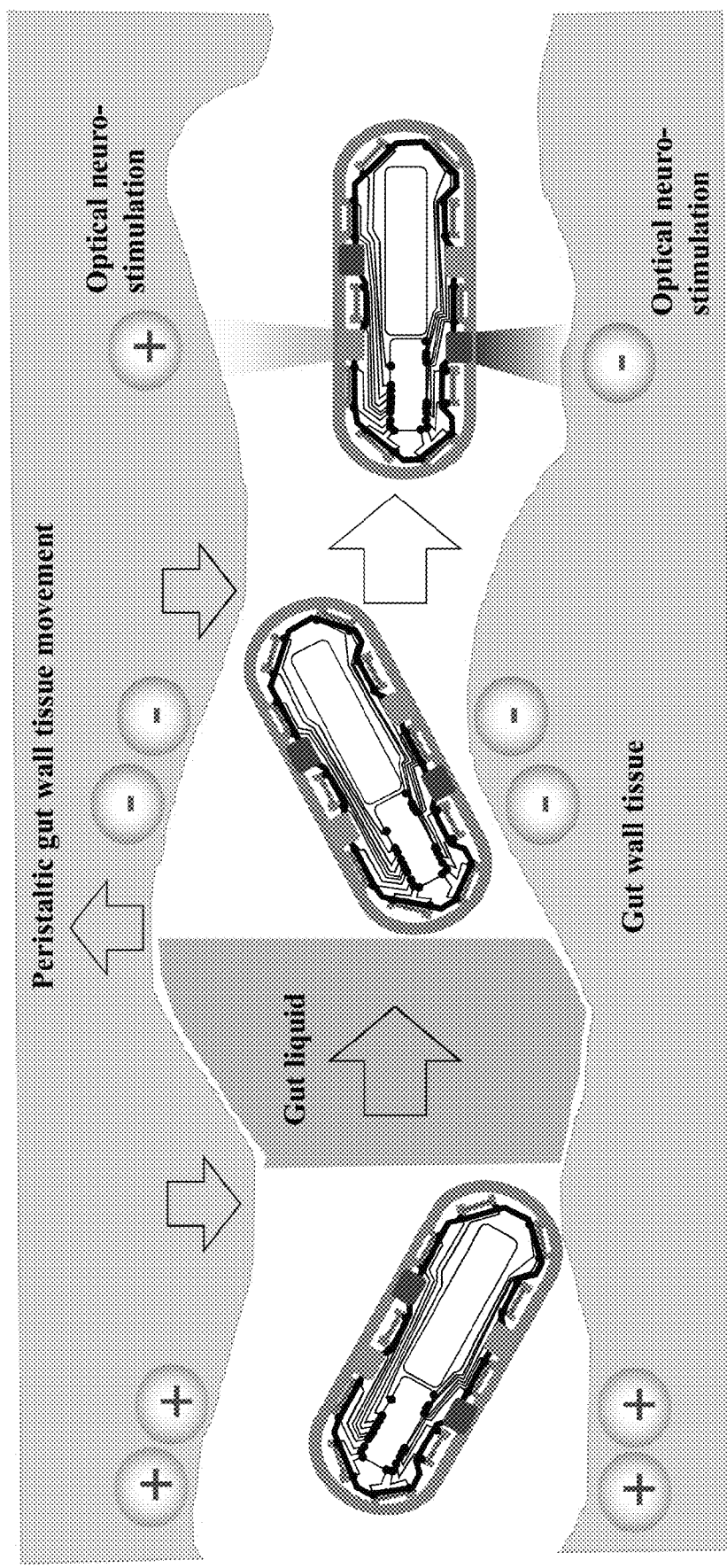
FIG. 13 illustrates the movement of the capsule of an embodiment along the intestine and gut with a peristaltic pumping movement of the gut, and the optical neuro-stimulation of the gut tissue cells.

As shown in FIG. 13, the capsule is naturally moving along the whole intestine and gut with a peristaltic pumping movement of the gut. The different PC-HEMTs within the same capsule are exposed in a different manner to the gut wall tissue charges and to their neuronal signalling, thereby mapping the functional neuro-peristaltic activity along the whole gut. In order to interact with the gut neuron cells and activate them, the capsule contains at least one pair of light-emitting diodes (LEDs) irradiating the gut at different wavelengths, for example yellow and blue. The different wavelengths can effectively stimulate higher neuronal potentials on the gut walls.

In a further embodiment, the PC-HEMT's surface can be functionalised with different biomarkers making it possible to explore the gut tissue based on its optogenetic activity by tracing epi-genetic (nutrigenetic) changes.

In yet further embodiment, the method for a gastrointestinal tract diagnosis and gut motility monitoring comprises the following steps:

1) Introducing the swallowable capsule of the embodiments into an unmodified gastrointestinal tract of a patient;
2) Recording electrical signals received from the gastrointestinal tract of the patient with the charge-sensitive and pressure-sensitive transistors in a form of a source-drain electric current of said transistors over time (defined as IDS dynamics);
3) Processing and converting said signals to digital signals;
4) Wirelessly transmitting said digital signals to a receiver unit; and
5) Processing the transmitted signals in the receiver unit, correlating said $I_{DS}$ dynamics with the peristaltic tissue cycles and obtaining a neuro-peristaltic activity spectrum, thereby providing medical information on the gut motility and GI tract condition.

In some embodiments, said neuro-peristaltic activity spectrum and corresponding medical information is further displayed in form of a visual, graphical or mathematical representation of the $I_{DS}$ dynamics or any other readable format. In a particular embodiment, the step of wirelessly transmitting said digital signals to the receiver unit is performed by either a zero-power digital NFC module or by a battery-powered digital NFC module.

EXAMPLES

Gut Tumour Diagnostics in Mice

Carcinogenic neoplasms and malignomas within a colon, small intestine and stomach cause dysfunctions of the peristalsis and neuronal signalling. Consequently, they can be subjected to single-point diagnostics using the PC-HEMT sensor of some embodiments of the present application. A series of measurements on a mouse gut were performed with the prototype sensor of the application for proving feasibility towards the capsule-based gut diagnostics. These experiments include measurements on a surgically operated gut of a mouse with the gut artery input control for different drugs, such as lidocaine, nifedipin, nicotine and glutamate, which may cause proliferation.

Figure 14:
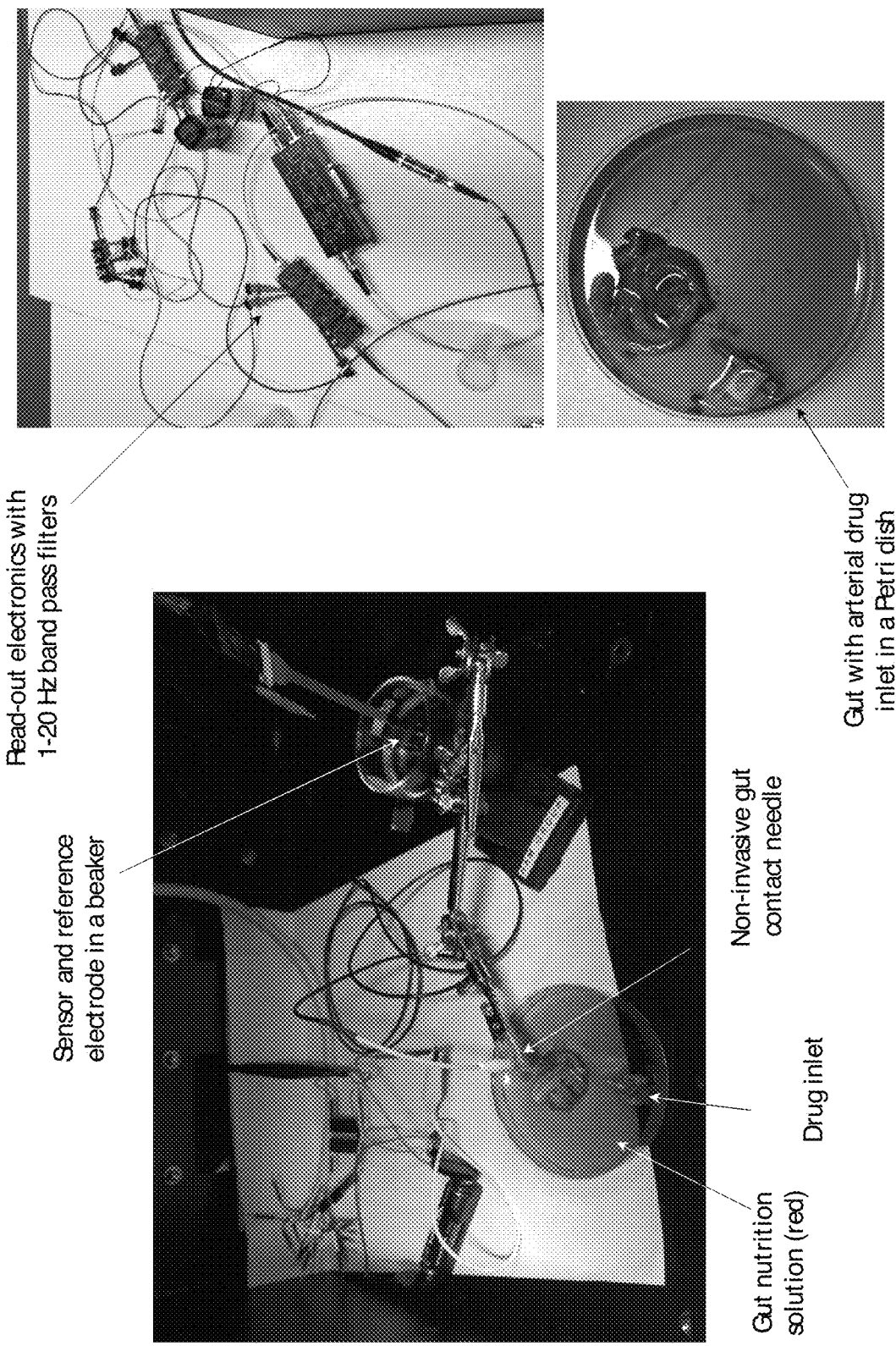
FIG. 14 shows the experimental PC-HEMT-based sensor setup for gut tumour diagnostics in mice.
Figure 15:
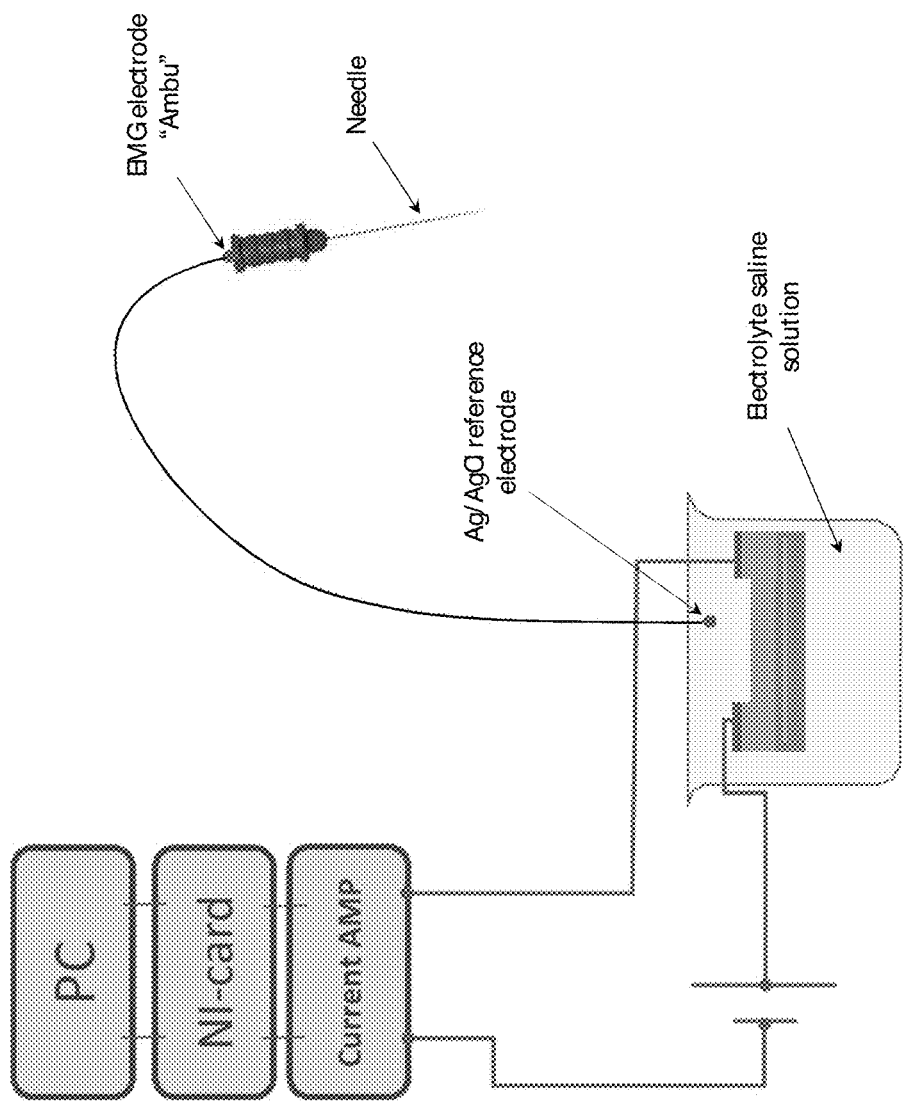
FIG. 15 schematically shows the PC-HEMT-based sensor setup of FIG. 14.

As shown in FIG. 14, the gut extracted from a mouse was placed in a nutrition solution in a Petri dish with a drug inlet inside. The PC-HEMT sensor was placed into a beaker filled with water and connected to the gut via a needle. The needle was inserted in the Petri dish close to the gut, non-invasively contacting the gut. The Ag/AgCl reference electrode was place in the same beaker near the sensor. The readout was performed with a 1-20 Hz band pass filter. FIG. 15 schematically shows this sensor setup.

FIG. 16a shows the results of the single-point non-invasive measurements of the mouse gut without a medicament supply, while FIG. 16b shows the results of the same measurements but with a medicament supply. The medicament causes the dysfunction similar to a carcinogenic action. The measurements without the medicament supply show the healthy peristaltic tissue cycles indicating the healthy neuro-peristaltic activity. However, once the medicament is supplied in the Petri dish, the measurements show the shapeless local gut fibrillations indicating the neuro-peristaltic activity dysfunctions similar to carcinogenic.

FIG. 17a shows two Fourier spectra recorded with the PC-HEMT sensor from the gut of a mouse without the medicaments added. FIG. 17b shows the same Fourier spectra with the addition of nifedipin and lidocaine for deactivation of a muscle and neuronal activity. The difference between the obtained spectra with and without the medicaments is clearly visible.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. A swallowable capsule for intestinal and gut diagnostics and gut motility monitoring comprising:
   1) a charge-sensitive pseudo-conductive high-electron mobility transistor (defined hereinafter as "charge-sensitive transistor"), or an array thereof, for detection of gut tissue potentials created from neuronal signaling or from muscular peristaltic tissue potentials, said charge-sensitive transistor comprising:
      a) a multilayer hetero-junction structure made of gallium nitride (GaN) and aluminium gallium nitride (AlGaN) single-crystalline or polycrystalline semiconductor materials, said multilayer hetero-junction structure comprising at least one buffer layer and at least one barrier layer, said layers being stacked alternately, and said multilayer hetero-junction structure being deposited on a substrate layer;
      b) a conducting channel comprising a two-dimensional electron gas (2DEG) or a two-dimensional hole gas (2DHG), formed at an interface between said buffer layer and said barrier layer and providing electron or hole current in said transistor between source and drain contacts;
      c) the source and drain contacts connected to said 2DEG or 2DHG conducting channel and to electrical metallizations for connecting said transistor to an electric circuit; and
      d) an open gate area between said source and drain contacts; and
   2) a pressure-sensitive pseudo-conductive high-electron mobility transistor (defined hereinafter as "pressure-sensitive transistor"), or an array thereof, for detection of changes in gut pressure, said pressure-sensitive transistor comprising:
      a) a multilayer hetero-junction structure made of gallium nitride (GaN) and aluminium gallium nitride (AlGaN) single-crystalline or polycrystalline semiconductor materials, said multilayer hetero-junction structure comprising at least one buffer layer and at least one barrier layer, said layers being stacked alternately, and said multilayer hetero-junction structure being placed on free-standing membranes;
      b) a conducting channel comprising a two-dimensional electron gas (2DEG) or a two-dimensional hole gas (2DHG), formed at the interface between said buffer layer and said barrier layer and providing electron or hole current in said transistor between source and drain contacts;
      c) the source and drain contacts connected to said 2DEG or 2DHG conducting channel and to electrical metallizations for connecting said transistor to an electric circuit; and
      d) an open gate area between said source and drain contacts; and
   said charge sensitive or pressure-sensitive transistor is characterised in that a thickness of the top layer of said multilayer heterojunction structure in the open gate area of any one of said charge-sensitive or pressure-sensitive transistors is 5-9 nanometres (nm) and the surface of said top layer has a roughness of 0.2 nm or less, wherein a combination of said thickness and said roughness of the top layer creates a quantum electronic effect of operating said 2DEG or 2DHG channel simultaneously in both normally-on and normally-off operation modes of the channel, thereby making said transistor to conduct electric current through said channel in a quantum well between normally-on and normally-off operation modes of the transistor.

2. The swallowable capsule of claim 1, wherein said charge-sensitive and pressure-sensitive transistors, or arrays thereof, are installed on a flexible printed circuit board (PCB), wherein each one of said charge-sensitive and pressure-sensitive transistors is connected to a microcontroller via its dedicated electrical contact line printed on said PCB.

3. The swallowable capsule of claim 2, further comprising:
   1) at least one pair of light-emitting diodes (LEDs) installed on said PCB for irradiating surrounding tissue of an intestine and gut with two different wavelengths of light, thereby stimulating neuronal activity of tissue cells, which is sensed by said charge-sensitive transistors;
   2) the microcontroller with a digital-to-analogue (DAC) and analogue-to-digital (ADC) converter for recording and processing signals received from said charge-sensitive and pressure-sensitive transistors;
   3) a battery unit connected to said dedicated electrical contact lines via an electric circuit for supplying electric current to said PCB;
   4) an integrated or CMOS current amplifier connected to said battery unit for amplification of an electric current obtained from said charge-sensitive and pressure-sensitive transistors;
   5) a connection module for wirelessly and remotely connecting said swallowable capsule to a receiver unit; and
   6) a cylindrically-shaped and light transparent housing configured to wrap of said swallowable capsule up, wherein said housing is made of an ion-permeable biocompatible membrane.

4. The swallowable capsule of claim 1, wherein said charge-sensitive and pressure-sensitive transistors, or arrays thereof, are installed on a flexible PCB, wherein each one of said charge-sensitive and pressure-sensitive transistors is connected to a DAC via its dedicated electrical contact line printed on said PCB.

5. The swallowable capsule of claim 4, further comprising:
  1) at least one pair of LEDs installed on said PCB for irradiating surrounding tissues of an intestine and gut with two different wavelengths of light, thereby stimulating neuronal activity of tissue cells, which is sensed by said charge-sensitive transistors;
  2) said DAC for converting alternating current (AC) signals received from said charge-sensitive and pressure-sensitive transistors to direct current (DC) signals;
  3) an ADC for processing analogue signals received from said DAC and converting said analogue signals to the digital signals for transmitting said digital signals to a receiver unit;
  4) at least one pair of antennas for wirelessly transmitting said digitals signals to said receiver unit; and
  5) a cylindrically-shaped and light transparent housing for wrapping the components of said swallowable capsule up, wherein said housing is made of an ion-permeable biocompatible membrane;
  wherein said DAC together with said ADC and said antennas constitute a zero-power digital near-field communication (NFC) module for wireless communication with said receiver unit.

6. The swallowable capsule of claim 1, wherein said charge-sensitive and pressure-sensitive transistors, or arrays thereof, are installed on a flexible PCB, wherein each one of said charge-sensitive and pressure-sensitive transistors is powered by a battery unit via its dedicated electrical contact line printed on said PCB.

7. The swallowable capsule of claim 6, further comprising:
  1) at least one pair of LEDs installed on said PCB for irradiating surrounding tissue of an intestine and gut with two different wavelengths of light, thereby stimulating neuronal activity of tissue cells, which is sensed by said charge-sensitive transistors;
  2) said battery unit connected to said dedicated electrical contact lines via an electric circuit for supplying electric current to the components of said swallowable capsule;
  3) an ADC for processing analogue signals received by said swallowable capsule and converting said analogue signals to digital signals for transmitting said digital signals to a receiver unit;
  4) at least one pair of antennas for wirelessly transmitting said digitals signals to said receiver unit; and
  5) a cylindrically-shaped and light transparent housing configured to wrap said swallowable capsule up, wherein said housing is made of an ion-permeable biocompatible membrane;
  wherein said ADC together with said battery unit and said antennas constitute a battery-powered digital NFC module for wireless communication with said receiver unit.

8. The swallowable capsule of claim 3, wherein said receiver unit is a smartphone, cardphone, smartwatch or any other similar mobile device, a desktop computer, server, remote storage, internet storage or telemedicine cloud.

9. The swallowable capsule of claim 1, wherein the multilayer hetero-junction structure of any one of said charge-sensitive or pressure-sensitive transistors comprises a single buffer layer and a single barrier layer.

10. The swallowable capsule of claim 1, wherein the multilayer hetero-junction structure of any one of said charge-sensitive or pressure-sensitive transistors comprises one top buffer layer, one barrier layer and one bottom buffer layer, said barrier layer being placed between said top and bottom buffer layers, and the two-dimensional electron gas (2DEG) conducting channel is formed in said top buffer layer above the barrier layer, close to the interface between said top buffer layer and said barrier layer, thereby resulting in a N-face polarity of said transistor.

11. The swallowable capsule of claim 1, wherein the multilayer hetero-junction structure of any one of said charge-sensitive or pressure-sensitive transistors comprises one top buffer layer, one barrier layer and one bottom buffer layer, said barrier layer being placed between said top and bottom buffer layers, and the two-dimensional hole gas (2DHG) conducting channel is formed in said top buffer layer above the barrier layer, close to the interface between said top buffer layer and said barrier layer, thereby resulting in a Ga-face polarity of said transistor.

12. The swallowable capsule of claim 1, wherein the source and drain contacts of said transistor are ohmic.

13. The swallowable capsule of claim 1, wherein the source and drain contacts of said transistor are non-ohmic.

14. The swallowable capsule of claim 13, wherein the electrical metallizations of the transistor are capacitively coupled to the 2DEG or 2DHG conducting channel for inducing displacement currents, thereby creating said non-ohmic source and drain contacts.

15. The swallowable capsule of claim 1, wherein any one of said charge-sensitive or pressure-sensitive transistors further comprises a dielectric layer deposited on top of the multilayer hetero junction structure.

16. The swallowable capsule of claim 15, wherein said dielectric layer comprises SiO—SiN—SiO ("ONO") stack or SiN—SiO—SiN ("NON") stack of 100-100-100 nm thickness.

17. The swallowable capsule of claim 1, wherein the substrate layer of the charge-sensitive transistor comprises sapphire, silicon, silicon carbide, gallium nitride or aluminium nitride.

18. The swallowable capsule of claim 1, wherein the thickness of the top layer (barrier or buffer) of any one of said charge-sensitive or pressure-sensitive transistors in the open gate area is 6-7 nm.

19. The swallowable capsule of claim 18, wherein the thickness of said top layer in said open gate area is 6.2 nm to 6.4 nm.

20. The swallowable capsule of claim 18, wherein said top layer has the roughness of about 0.1 nm or less, or 0.05 nm or less.

21. The swallowable capsule of claim 1, wherein the free-standing membranes, on which the multilayer hetero junction structure of the pressure-sensitive transistor is placed, are free-standing columns of substrate composed of sapphire, silicon, silicon carbide, gallium nitride or aluminium nitride.

22. The swallowable capsule of claim 21, wherein said substrate is gallium nitride (GaN) having thickness of 0.5-2 μm.

23. The swallowable capsule of claim 1, wherein any one of said charge-sensitive or pressure-sensitive transistors further comprises an excitation light source for irradiating the multilayer hetero-junction structure, thereby inducing an electric current in the 2DEG or 2DHG conducting channel.

24. The swallowable capsule of claim 23, wherein said excitation light source is a laser diode or LED.

25. The swallowable capsule of claim 1, wherein said multilayer hetero-junction structure comprises:
  A. (i) one top AlGaN layer recessed in an open gate area of the transistor to the thickness of 5-9 nm and having the surface roughness of 0.2 nm or less, and (ii) one bottom GaN buffer layer; said layers have Ga-face polarity, thus forming the two-dimensional electron gas (2DEG) conducting channel in said GaN layer, close to the interface with said AlGaN layer; or B. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have Ga-face polarity, thus forming a two-dimensional hole gas (2DHG) conducting channel in the top GaN layer, close to the interface with said AlGaN barrier layer; or C. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have N-face polarity, thus forming a two-dimensional electron gas (2DEG) conducting channel in the top GaN layer, close to the interface with said AlGaN barrier layer; or D. (i) one top AlGaN layer recessed in an open gate area of the transistor to the thickness of 5-9 nm and having the surface roughness of 0.2 nm or less, and (ii) one bottom GaN buffer layer; said layers have N-face polarity, thus forming a two-dimensional hole gas (2DHG) conducting channel in the GaN buffer layer, close to the interface with said AlGaN barrier layer.

26. A method for a gastrointestinal (GI) tract diagnosis and gut motility monitoring, comprising:
1) Introducing the swallowable capsule of claim 1 into an unmodified gastrointestinal tract of a patient;
2) Recording electrical signals received from the gastrointestinal tract of the patient with the charge-sensitive and pressure-sensitive transistors in a form of a source-drain electric current of said transistors over time (defined as IDS dynamics);
3) Processing and converting said signals to digital signals;
4) Wirelessly transmitting said digital signals to a receiver unit; and
5) Processing the transmitted signals in the receiver unit, correlating said IDS dynamics with peristaltic tissue cycles and obtaining a neuro-peristaltic activity spectrum, thereby providing medical information on the gut motility and GI tract condition.

27. The method of claim 26, wherein the step of wirelessly transmitting said digital signals to said receiver unit is performed by either a zero-power digital NFC module or by a battery-powered digital NFC module.

28. The method of claim 26, wherein said neuro-peristaltic activity spectrum and corresponding medical information is further displayed in form of a visual, graphical or mathematical representation of the IDS dynamics or any other readable format.

* * * * *